United States Patent [19]

Albert et al.

[11] Patent Number: 4,947,857

[45] Date of Patent: Aug. 14, 1990

[54] METHOD AND APPARATUS FOR ANALYZING AND INTERPRETING ELECTROCARDIOGRAMS USING SPECTRO-TEMPORAL MAPPING

[75] Inventors: David E. Albert, McAlester; Paul Lander, Norman, both of Okla.

[73] Assignee: Corazonix Corporation, Oklahoma City, Okla.

[21] Appl. No.: 305,293

[22] Filed: Feb. 1, 1989

[51] Int. Cl.⁵ .............................................. A61B 5/04
[52] U.S. Cl. .................................... 128/696; 128/710
[58] Field of Search ............... 128/696, 699, 702, 703, 128/704, 705, 706, 708, 710

[56] References Cited

U.S. PATENT DOCUMENTS

| | | | |
|---|---|---|---|
| 3,605,727 | 9/1971 | Zenevich et al. | 757/346 |
| 3,822,696 | 7/1974 | Ekstrom et al. | 184/716 |
| 4,023,564 | 5/1977 | Valiquette et al. | 652/622 |
| 4,085,407 | 4/1978 | Stratbucker et al. | 681/138 |
| 4,115,864 | 9/1978 | Vick et al. | 791/559 |
| 4,157,711 | 6/1979 | Votam et al. | 890/240 |
| 4,422,459 | 12/1983 | Simson | 353/538 |
| 4,458,691 | 7/1984 | Netravall | 347/916 |
| 4,458,692 | 7/1984 | Simson | 347/989 |
| 4,492,235 | 1/1985 | Sitrick | 347/988 |
| 4,630,204 | 12/1986 | Mortara | 582/225 |
| 4,665,485 | 5/1987 | Lundy et al. | 128/699 |
| 4,697,597 | 10/1987 | Sanz et al. | 128/699 |
| 4,732,158 | 3/1988 | Sadeh | 128/702 |

OTHER PUBLICATIONS

Berbari, E. J. et al., "The His–Purkinje Electrocardiogram in Man", *Circulation*, vol. 54, No. 2 (Aug. 1976), pp. 219–224.

Berbari, E. J. et al., "A Computerized Technique to Record New Components of the Electrocardiogram", *Proceedings of IEEE*, vol. 65, No. 5, (May 1977), pp. 799–802.

Berbari, E. J. et al., "Recording from the Body Surface of Arrhythmogenic Ventricular Activity During the S–T Segment", *American Journal of Cardiology*, vol. 41 (Apr. 1978), pp. 697–702.

Berbari, E. J., "New Engineering Approaches to Noninvasive His–Purkinje System Recordings", Ph. D. Dissertation, University of Iowa (May 1980).

Breithardt, G. et al., "Clinical Significance of Ventricular Late Potentials", *Signal Averaging Technique in Clinical Cardiology*, (May 1981), pp. 219–232.

Chien, I-C. et al., "Computer Methods for Analyzing the Highfrequency Electrocardiogram", *Medical & Biological Engineering & Computer*, vol. 18, No. 3 (May 1980), pp. 303–312.

Fontaine, G. et al., "High Amplification Electrocardiography in Cardiac Arrhythmias and Conduction Defects", *High Amplification Electrocardiography*, (Sep. 1979), pp. 227–301.

Hopp, H. W. et al., "Ventricular Delayed Depolarizations in Patients with Chronic Stable Coronary Heart Disease and with Acute Myocardial Infarction", *Signal Averaging Technique in Clinical Cardiology*, (May 1981), pp. 233–252.

Kormylo, J. J. et al., "Two–Pass Recursive Digital Filter with Zero Phase Shift", *IEEE Trans. Acous. Speech and Signal Proc.*, vol. 22, No. 5 (Oct. 1974, pp. 384–387.

(List continued on next page.)

*Primary Examiner*—Francis Jaworski
*Assistant Examiner*—George Manuel
*Attorney, Agent, or Firm*—Hubbard, Thurman, Turner, Tucker & Harris

[57] ABSTRACT

Method and apparatus for analyzing ECG signal data for diagnostic purposes by performing an incrementally moving, short window FFT analysis to produce a set of spectral templates representative of the spectral frequency content of the ECG at each window position. The spectral templates may be displayed as a representation of a three dimensional surface or mathematically analyzed. The changes in the shape of the templates or surface with time represent a change in the spectrum, which are shown to be an indication of abnormalities in the heart.

28 Claims, 14 Drawing Sheets

OTHER PUBLICATIONS

Longini, R. L. et al., "Filtering without Phase Shift, IEEE Transactions on Biomedical Engineering", vol. 22, No. 5 (May 1977), pp. 707–713.

Santopietro, R. F., "The Origin and Characterization of the Primary Signal, Noise, and Interference Sources in the High Frequency Electrocardiogram", Proceeding of IEEE, vol. 65, No. 5 (May 1977) pp. 707–713.

Simson, M. B. et al., "Late Potentials in Man and Cardiac Arrhythmias", *Signal Averaging Technique in Clinical Cardiology*, (May 1981), pp. 253–264.

Simson, M. B., "Use of Signals in the Terminal QRS Complex to Identify Patients with Ventricular Tachycardia after Myocardia Infarction", *Signal Averaging Technique in Clinical Cardiology*, (May 1981), pp. 235–242.

Jijen, G. J. H. et al., "Accuracy of QRS Detection in Relation to the Analysis of High–Frequency Components in the Electrocardiogram", *Medical & Biological Engineering & Computer*, vol. 17, No. 4 (Jul. 1979), pp. 492–502.

Uther, J. B. et al., "The Detection of Delayed Activation Signals of Low Amplitude in the Vectorcardiogram of Patients with Recurrent Ventricular Tachycardia by Signal Averaging", Proceedings of Symposium: Management of Ventricular Tachycardia–Role of Mexiletine (May 1978), pp. 80–82.

Weaver, C. S. et al., "Digital Filtering with Applications to Electrocardiogram Processing", IEEE Transactions on Audio and Electroacoustics, vol. 16, No. 3 (Sep. 1968), pp. 350–391.

Panel Discussion by Alconcourt, Berbari and Fontaine, *Signal Averaging Technique in Clinical Cardiology*, (May 1981), pp. 265–272.

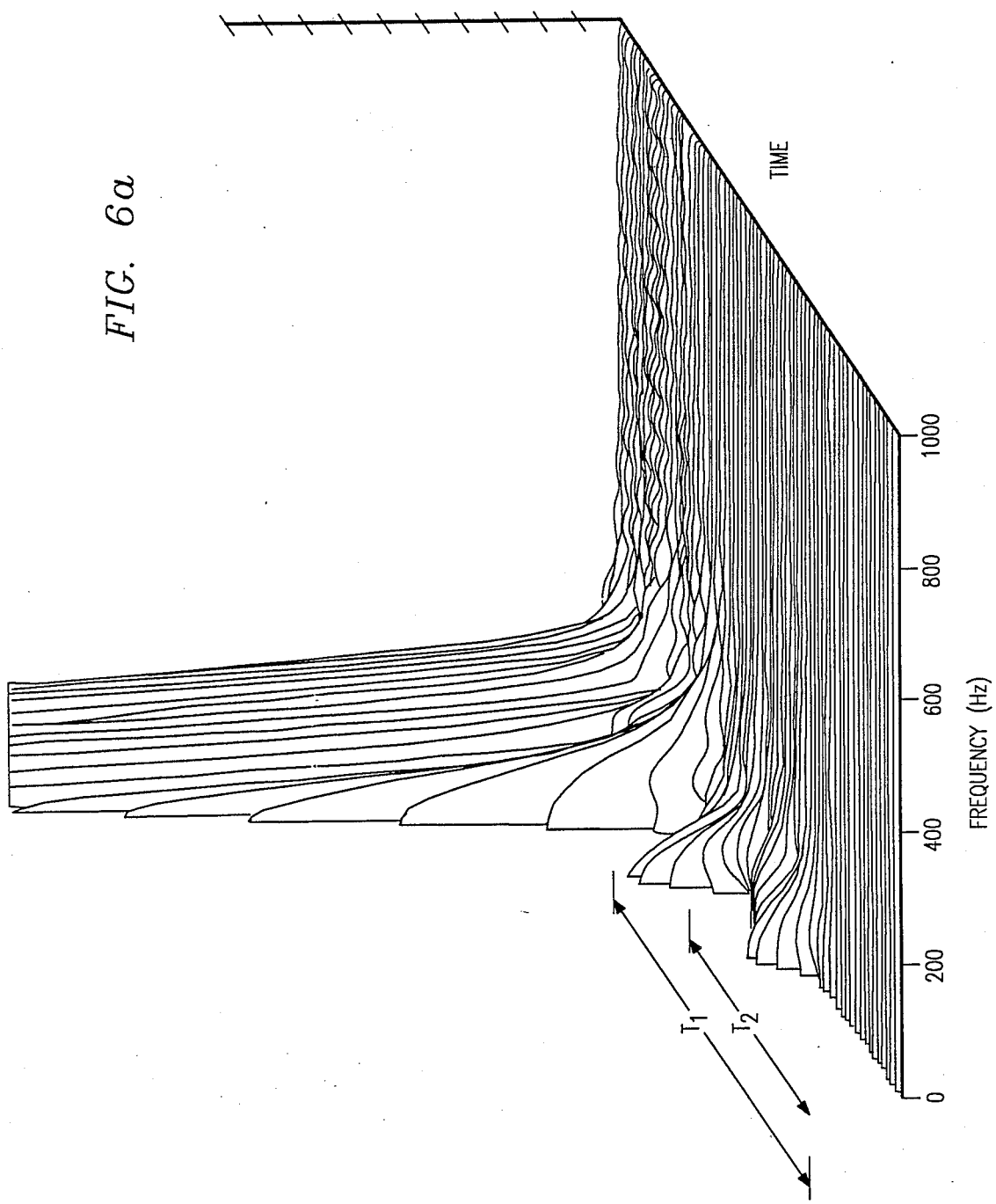

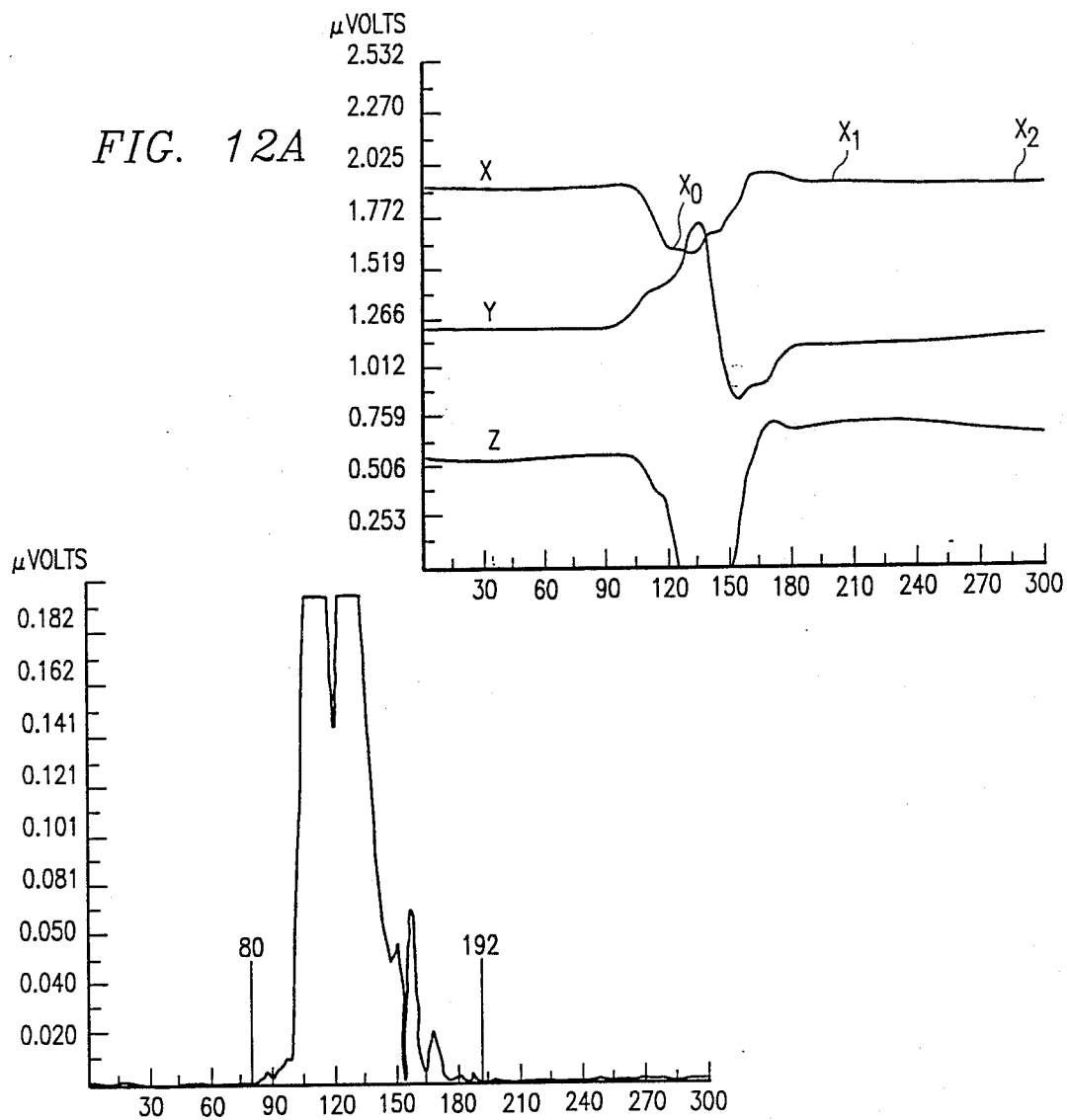
FIG. 12A
FIG. 12B
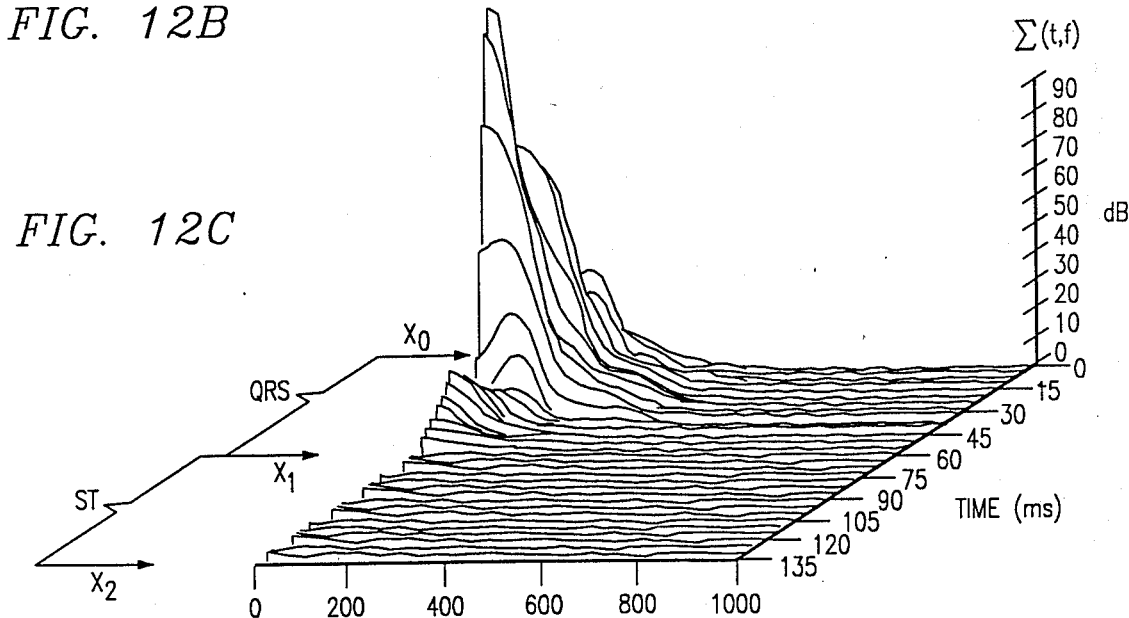
FIG. 12C

METHOD AND APPARATUS FOR ANALYZING AND INTERPRETING ELECTROCARDIOGRAMS USING SPECTRO-TEMPORAL MAPPING

This invention relates generally to the art of determining the condition of a human heart by either invasive or noninvasive electrocardiograms (ECG), and more particularly relates to method and apparatus for processing ECG signals in both the time and frequency domain to produce a three dimensional surface representative of the ECG (Spectro-Temporal Map STM). The three dimensional surface has three axes representing time, frequency and spectral amplitude. The three dimensional surface presentation is particularly useful for visually and/or automatically determining the presence of ventricular late potentials which are know to be indicative of a tendency toward ventricular tachycardia, as well as other evaluations of the ECG data.

BACKGROUND OF THE INVENTION

Sudden death from acute arrhythmia is a significant risk after myocardial infarction. The risk is great immediately after infarction, and tapers downwardly with the passage of time, although approximately fifty percent of all patients eventually die of ventricular arrhythmia.

It has been determined by numerous investigators that high frequency potentials in the late QRS and ST segments of electrocardiograms is a good indicator of patients at risk of acute arrhythmia. These late potentials have been shown to be characterized by frequencies between about 10 and 250 Hz, and tend to occur in a short time period at the end of the normal QRS segment, with the result that the apparent length of the QRS signal is extended for these patients. However, late potentials are very difficult to detect because of the magnitude of the late potential voltage signals are approximately the same as the typical noise of a raw ECG signal. Detection is further complicated by the intermingling with and close proximity to the QRS segment which is many times greater in amplitude. This problem is further aggravated in patients suffering from bundle branch block which extends the high amplitude portion of the QRS function out into the time period where the late potentials occur.

U.S. Pat. No. 4,422,459, issued to Simson, discloses a method and apparatus for detecting late potentials by signal averaging multiple samples of electrocardiographic signals, typically the conventional X, Y, and Z leads, or the vector sum of these signals to produce a high resolution electrocardiogram (HRECG). A high pass filter is then applied in reverse order to the HRECG. The reverse filtering of latter portion of the QRS segment prevents the ringing artifact which would otherwise result from filtering the high amplitude QRS signal in the forward direction, which would obscure the small amplitude late potentials. The end of the QRS segment, including late potentials, is detected, the RMS of the filtered function over the last 40 milliseconds is computed, and compared to a predetermined RMS value. If the RMS value is less than the predetermined value, it is assumed that late potentials exist, and if the RMS is greater than the predetermined value, it is assumed that no late potentials exist because the 40 millisecond period is actually the end portion of a normal high amplitude QRS section which has a much higher RMS value. Thus, the Simson method is dependent upon the time separation of the late potentials from the main QRS function. Since bundle branch block extends the main QRS event into the region where late potentials occur, this technique cannot be used. Further, the Simson method is not capable of detecting the termination of the normal QRS segment or the independent determination of the onset of the late potentials should they be intermingled with the normal QRS segment.

Because of the limitations on the Simson method, others have attempted to detect late potentials using more direct nonfiltered methods. These efforts have primarily centered around attempts to frequency analyze the HRECG using Fourier analysis by Cain. Initial reports of successful results have not been corroborated by other researchers (Gomes et al, Worley et al, Kelen et al), and there are theoretical reasons why such approaches are not possible as will be more fully developed hereafter.

SUMMARY OF THE INVENTION

We have discovered that an ECG indicative of an abnormal heart frequently has time variant changes of the frequency spectrum. More emphatically, the QRS segment of a normal, healthy heart has a substantially constant frequency with respect to time while defects in the heart tend to cause variations in the spectrum of the QRST segments with respect to time. As a result, the ECG from a human can be very advantageously analyzed, visually and automatically, by processing the ECG to produce data representative of a three dimensional surface defined by three coordinate axes which represent the real time of the HRECG, the spectral content, and the relative amplitude or power of the spectral components expressed in appropriate terms such as signal amplitude (volts) or power. The spectral estimates for each time interval are derived by applying a relatively short time period window, i.e., 12 to 32 milliseconds to the HRECG waveform and performing spectrum analysis on the HRECG signal within the window using, for example, a Fast Fourier Transform. The window is incremented a much shorter time interval, typically 2 milliseconds, along the HRECG and the FFT transform repeated. When this data is visually displayed in a three dimensional mode, it provides spectral information with respect to time, and thus is referred to as an electrocardiogram spectro-temporal map (ECGSTM). In particular, when visually presented as a series of spectral templates each having a shape representing the spectral content of the ECG at the corresponding point in time, a physician is presented with a graphic and readily apparent indication of the presence of high frequency, low amplitude signals within the ECG, including late potentials standing in the ST segment which appear to prolong the QRS, as well as those partially intermingled with the QRS segment. The three dimensional surface can also be represented by contour lines of constant time, frequency or amplitude, and these contour lines define sets of "templates" which are convenient means of presenting a large amount of data useful in mathematically quantifying the HRECG for clinical purposes.

It has been determined through analysis of clinical data that the normal QRS segment has a relatively less time-varying spectrum than late potentials which exhibit multiple abrupt shape changes. These abrupt changes in the shape of successive spectra in templates along the time axis provide a basis, either visually or automatically, for detecting the onset and offset of the normal QRS, and also the onset and offset of late potentials.

In addition to analysis for detecting late potentials, the system provides a means for the graphic illustration of possible abnormalities occurring within the major QRS event which produce time variant changes in the frequency spectrum of an ECG.

The present invention also includes a system for gathering, processing and automatically making predetermined measurements of an ECG indicative of late potentials, and also for displaying the processed data in three dimensions, or as otherwise desired by the physician, to verify the automatically produced data, and to manually select data points from which the automatically calculated values can be verified, or additional values calculated.

Additional aspects, advantages and details of the present invention may be determined from the following detailed description of preferred embodiments, which are illustrated by the following drawings wherein:

BRIEF DESCRIPTION OF THE DRAWINGS

FIG. 4b is a schematic representation of the frequency spectrum analysis produced by a Fourier Transform of the signal illustrated in FIG. 4a;

FIG. 6a is an isometric three dimensional graphical representation of a surface illustrating data produced by processing the HRECG of FIG. 2 using the sliding window FFT embodiment of the present invention;

FIG. 6b illustrates a set of constant frequency templates derived from the data of FIG. 6a superimposed upon the plane containing the time and amplitude axes of FIG. 6a;

FIG. 6c illustrates a set of constant amplitude templates derived from the data of FIG. 6a superimposed upon the plane of the time and frequency axes of FIG. 6a;

FIG. 8 is a schematic graphical representation of a correlation coefficient derived by comparing adjacent spectral templates illustrated in FIG. 6a;

FIGS. 9a and 9b are schematic three dimensional graphical representations of the geometric differences in the spectral templates illustrated in FIG. 6a;

FIG. 10 is a schematic graphical representation of the spectral edge and median frequency of the spectral templates illustrated in FIG. 6a;

FIGS. 11c and 11d are schematic representations of the set of constant frequency and constant amplitude templates, respectively, derived from the surface data represented by FIG. 11a;

FIG. 12a is a schematic graphical representation of the X, Y and Z leads of a HRECG;

FIG. 12b is a schematic graphical representation of a bidirectionally, high pass filtered, vector sum of the X, Y and Z HRECG signals of FIG. 12a which indicates the absence of late potentials using accepted clinical criteria;

FIG. 12c is a schematic representation of a spectrotemporal map of the X lead HRECG of FIG. 12a produced in accordance with the present invention which indicates the presence of late potentials;

FIG. 13b is a schematic spectro-temporal map in accordance with the present invention of the HRECG used to produce the graph of FIG. 13a;

DETAILED DESCRIPTION

Figure 1:
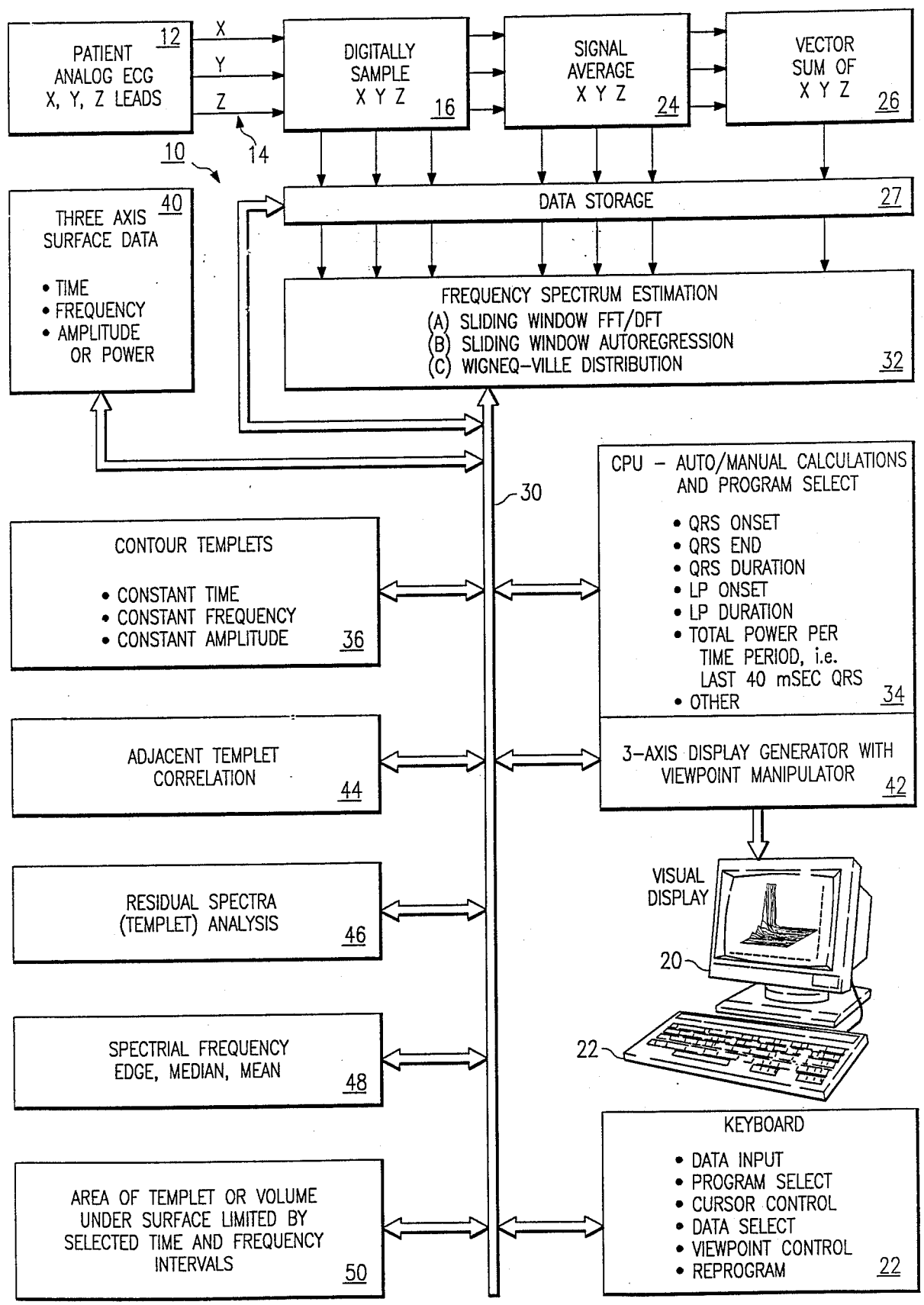
FIG. 1 is a block diagram of a digital system in accordance with the present invention which is particularly suited to carry out the method of the present invention.

Referring now to the drawings, and in particular to FIG. 1, a system in accordance with the present invention for carrying out the method of the present invention is indicated generally by the reference numeral 10. The system 10 includes a conventional ECG analog system 12 including one or more electrodes to be positioned at any place on or within the body of a patient to sense and amplify electrical body signals originating in the heart. Although any number of electrodes may be used, it is more common to employ six which are ideally located at orthogonal positions on the body to produce ECG signals for the leads designated by X, Y and Z. These signals are collected and processed using suitable conventional amplification equipment, including typically an electrical analog low pass filter to eliminate high frequency noise. These three analog voltage signals with respect to real time are represented by lines 14. These X, Y, Z analog signals are applied to a conventional digital sampling system 16, which preferably samples each of the signals at a two thousand Hz rate, or once each 0.5 milliseconds, to produce a digitally represented amplitude value, typically representing millivolts. Each of the X, Y and Z lead ECG signals is digitized for a sufficient period of time to include as many as 500 QRST waveforms. Once the waveforms are in digital form, they may be processed by the remainder of the system 10.

Except for the analog hardware of the patient data collection system 12, and certain discrete designated digital processing components used in the digitizing system 16, system 10 is a specially programmed general purpose computer, preferably a portable lap-top computer, having a conventional keyboard 22, which includes the standard keyboard functions of data input, program select, reprogramming, three dimensional view pad control, and a display cursor control and related data select functions for the purposes which will presently be described.

The computer also includes a visual display screen 20, and conventional computer architecture including a central processing unit (CPU) 34, and digital storage for programs and data.

The remainder of the system 10 is of software defined to provide means for performing the various functions illustrated and hereafter described. The functional elements of the system are arranged around a data flow bus 30 which implies a free flow of all data between the CPU 34 and the memory in which data is stored. In general, the boxes to the left of the data bus 30 imply storage of data calculated by the CPU and which can be displayed or used for additional calculations at the command or stored procedure programs or by the operator through the keyboard.

The individual digitized X, Y and Z signals from block 16 can be signal averaged as represented by a block 24 to produce high resolution electrocardiogram (HRECG) signals using well known stacking techniques, such as that described in some detail in U.S. Pat. No. 4,422,459 previously referred to. In general, this process involves, for each X, Y and Z lead, selecting a large number of the 500 QRST waveforms for the respective lead signal, and in substance averaging the digital values at corresponding time points to significantly enhance the signal-to-noise ratio of each signal. The result is a single QRST waveform having digital values representing each 0.5 milliseconds sampling interval. The averaged signals of the X, Y and Z leads from block 24 can, if desired be combined to produce a vector sum signal as represented by block 26, again using conventional techniques such as described in the above-referenced patent 4,422,259. Any one or all of these seven signals may then be stored in memory as represented by data storage block 27 and accessed for all purposes directly by the CPU 34 by way of data bus 30.

The frequency spectrum estimator calculations can be made on any one of the seven ECG waveforms, i.e., any one of the original X, Y and Z digitized waveforms, the X, Y and Z signal averaged HRECG waveforms, or the vector sum waveform. The purpose of this frequency spectrum estimator is to generate data representing a three dimensional surface defined by time, frequency, and amplitude or power. Examples of the computational procedures which can be used for this purpose are as indicated in block 32, are the Sliding Window FFT/DFT procedure (SWFFT or SWDFT), the Sliding Window autoregressive procedure, or the procedure generally referred to as Wigner-Ville Distribution technique, which is a broader generalized approach to generating such surface data.

This data produced by the frequency spectrum estimator may conveniently be stored for further processing as Three Axis Surface Data in memory block 40. As mentioned, this basic information is accessible to all other data processing blocks of the system as represented by the various data flow lines 30. This surface data, when presented in a visual, three dimensioned surface provides a very significant analysis tool to a physician who must make decisions regarding treatment of the patient based on the information. Accordingly, the CPU 34 includes a three axis display generator and viewpoint manipulator, as represented by block 42 to display the surface data on the display screen 20 of the computer system. The viewpoint of the three axis display may preferably be rotated by the operator universally so that the viewpoint can be selectively aligned to view the surface representation from any angle. Of course, the image on the screen can also be printed out on hard copy for file records and the like.

The three dimensional surface data, by reason of the Frequency Spectral Estimation program, is in the form of a series of contour lines having constant time and defining an area between the surface and the plane of the time frequency axes, and the plane of the time-amplitude axes. Because of the importance of the "shape" of this area, which represents the spectral content of the ECG signal at that point in time, these areas are referred to as either "constant time" templates or "spectral templates. It is also useful to produce a set of constant frequency templates and also a set of constant amplitude templates in the same manner. These three sets of templates define sets of contour lines which can be displayed in any desired combination to present the three dimensional surface to the physician or other person analyzing the data, as will presently be described.

Although any of the evaluation procedures which will presently be described can be selectively performed automatically in response to a program, or in response to a manual command input from the keyboard, in virtually all cases a physician will confirm the results of any automatic computations by a visual reference to the surface or other data, and in many instances by manually selecting the data points from which various meaningful calculations to assist interpretation can be performed by the calculator program 34.

For example, one of the prime aspects of the present invention is the discovery that a normal ECG is made up of spectral templates of generally uniform shape throughout the QRS while late potentials and other variances of the ECG signal caused by abnormalities tend to have very differently shaped spectral templates. As a result, one of the primary analysis tools of the present invention relates to the observation and quantification of the variations in the frequency spectrum with respect to time, i.e., variations in the shapes of the spectral templates. The set of spectral templates are the primary tools for this analysis, but the constant frequency template and the constant amplitude templates can assist in a secondary manner. Accordingly, various analyses can be performed on any one of the contour templates developed by the program represented at 36, or the spectral templates generated by the program 32, and these are represented by the blocks designated Adjacent Template Correlation procedure 44, a Residual Spectral Analysis procedure 46, a Spectral Edge Median/Mean frequency of template area computation 48, and Area computation 50, each as will presently be described.

Frequency Spectrum Estimations

In accordance with one specific embodiment of the present invention, the frequency spectrum estimations are made for a given time on the ECG signal by performing a Fast Fourier Transform calculation using conventional techniques on the portion of the ECG signal contained within a selected short time segment, for example a 16 millisecond period centered about the given time which has been multiplied by any one of the well known window functions (i.e. Hamming). This procedure is repeated by effectively sliding the window by selected intervals, for example 2 milliseconds, and the procedure repeated. This is repeated to cover the entire QRST segment, or any desired portion thereof, to produce the set of data representative of the surface. The following discussion of Fourier transforms will assist one ordinarily skilled in the art in understanding and carrying out the present invention.

The Fourier transform in a classical sense, applies to deterministic, finite or continuous energy signals. The digitally sampled—or discrete—waveform, x(n), for n=0 to N-1, has a discrete Fourier transform (DFT) defined by $$x(k) = \sum_{n=0}^{N-1} x(n) \exp(-j2\pi nk/N) \quad [1]$$

where x(n) is the N-sample discrete waveform. The result of the discrete Fourier transform is the Fourier spectrum, X(k). This is defined for k=−N/2 to N/2−1. The value of X(k) at k=0 is termed the dc component, or 0Hz value. Values of X(k) for k=0 to N/2−1 are termed the 'positive frequence' values; values of X(k) for k=−N/2 to −1 are termed the 'negative frequency' values. The negative frequency values are a mirror image of the positive frequencies, hence only the latter are generally analyzed. The exponential term in equation [1] includes the constant j ($=\sqrt{-1}$), which implies that X(k) is a complex entity. Equation [1] can be re-written as $$X(k) = \sum_{n=0}^{N-1} x(n) (\cos(2\pi nk/N) - j \sin(2\pi nk/N)) \quad [2]$$

X(k) has a real part, consisting of the cosine terms, and an imaginary part, consisting of the sine terms. The inverse discrete Fourier transform of X(k) may be defined as $$x(n) = \sum_{k=0}^{N-1} S(k) \exp(j2\pi nk/N) \quad [3]$$

X(k) and x(n) are considered a Fourier transform pair because of this reciprocal relationship. From the complex Fourier spectrum X(k), we can compute phase, amplitude and power spectra. The phase spectrum, F(k), is defined as $$F(k) = \arctan(-Im(X(k))/R(X(k))) \quad [4]$$

where Im(X(k)) and R(X(k)) are the imaginary and real parts of X(k), respectively. The amplitude—or magnitude —spectrum, A(k), is defined as $$A(k) = |X(k)| \quad [5]$$

where | | denotes the modulus, or absolute value. The complex entity, X(k), has a modulus defined as $$|X(k)| = \sqrt{R(X(k))^2 + Im(X(k))^2} \quad [6]$$

The power spectrum, P(k), is defined as $$P(k) = |X(k)|^2 \quad [7]$$

The units of P(k) are actually power per Hz. Hence the actual power over any frequency band is found by rectangular integration of the area under P(k). For this reason P(k) is more properly called a power density spectrum (PDS). The inverse discrete Fourier transform of the PDS is the autocorrelation function, r(n)

$$r(n) = \sum_{k=0}^{N-1} P(k) \exp(j2\pi nk/N) \quad [8]$$

It should be noted that in computing P(k) the modulus of the Fourier spectrum is taken (cf. equation [6]). Hence the phase information (cf. equation [4]) is lost and it is not possible to reconstruct X(k) or x(n) from the PDS. The autocorrelation function and the PDS constitute a Fourier Transform pair.

Figure 3:
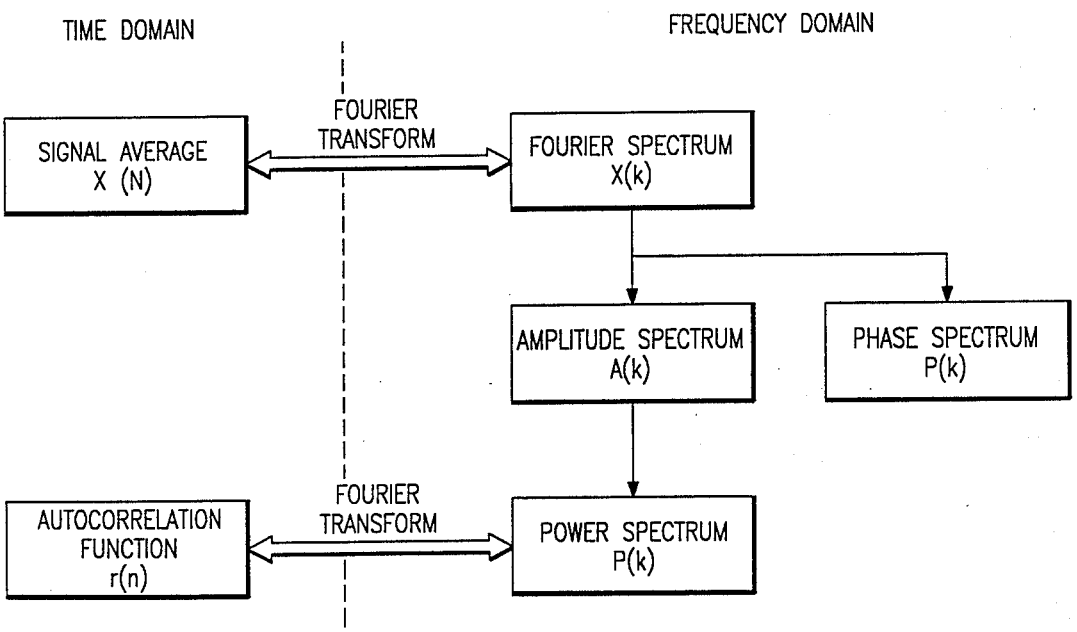
FIG. 3 is a block diagram illustrating the Fourier Transformations useful in carrying out the present invention.

The following basic Fourier Transform Properties will assist in understanding the present invention. The relationships between x(n), X(k), F(k), A(k) and P(k) and r(n) are illustrated in FIG. 3. There are a number of important properties of the discrete Fourier Transform. The two properties which are necessary to follow the discussions in this chapter are: (1) If two signals, c(n) and d(n), are summed the Fourier Transform is equal to the sum of the individual Fourier spectra of both.

$$\sum_{n=0}^{N-1} (c(n) + d(n)) \exp(-j2\pi nk/N) = C(k) + D(k) \quad [9]$$

A multiplication operation in the frequency domain is equivalent to a convolution in the time domain.

$$\sum_{n=0}^{N-1} (c(l) d(n + 1)) \exp(-j2\pi nk/N) = C(k) \cdot D(k) \quad [10]$$

for $l = 0$ to $N - 1$

For example, some types of digital filters are implemented by convolving the filter's impulse response with the signal in the time domain. This operation could be replaced by multiplying the Fourier spectra of the filter and the signal, and inverse transforming the product.

Often the quantities in the power spectrum are expressed on a decibel (db) scale where P(k) is given a value relative to $P_{max}(k)$ the maximum spectral value. This decibel value for each component of P(k) is given by decibel value of $$P(k) = 10 \log_{10}(P(k)/P_{max}(k))$$

Hence the decibel scale is a relative scale.

To summarize this introduction to Fourier analysis, it can be appreciated intuitively that a large number of different signals can be reconstructed using building blocks of sines and cosines. This finds a mathematical expression in the Fourier spectrum, which is found via the Fourier transform. From the Fourier transform result, one can move to the power density spectrum and measure spectral power by summing the spectrum over the frequency interval of interest. More detailed, information on the Fourier representation of signals, can be found in the introductory text "Signals and Systems" by Oppenheim and Willsky, Englewood Cliffs, N.J., Prentice-Hall, Inc. 1983 and "The FFT Fundamentals and Concepts" by Ramirez, Englewood Cliffs, N.J., Prentice-Hall, Inc., 1985.

Several processes may be selectively employed to improve the Fourier transformation in accordance with the present invention. These are referred to as windowing, dc removal, and zeropadding.

Figure 2:
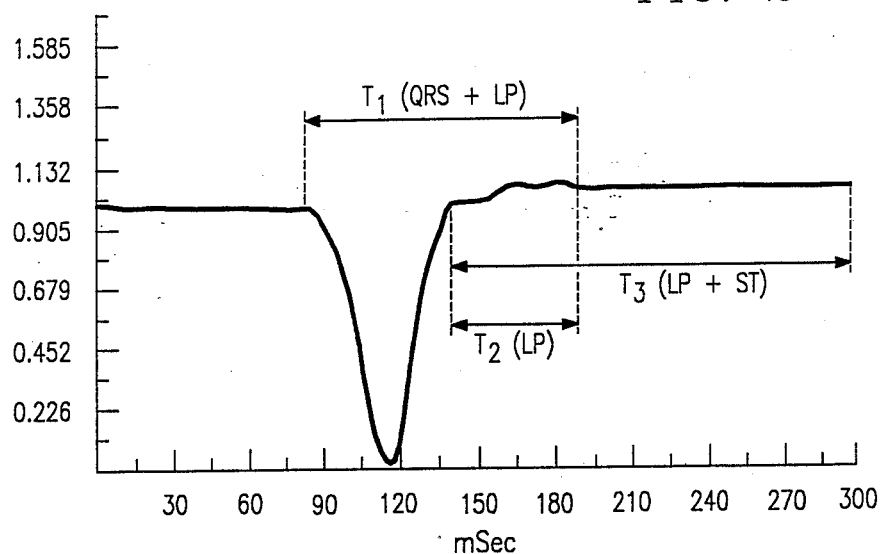
FIG. 2 is a schematic graph representation of a typical single lead ECG waveform which would be processed in accordance with the present invention.
Figure 4A:
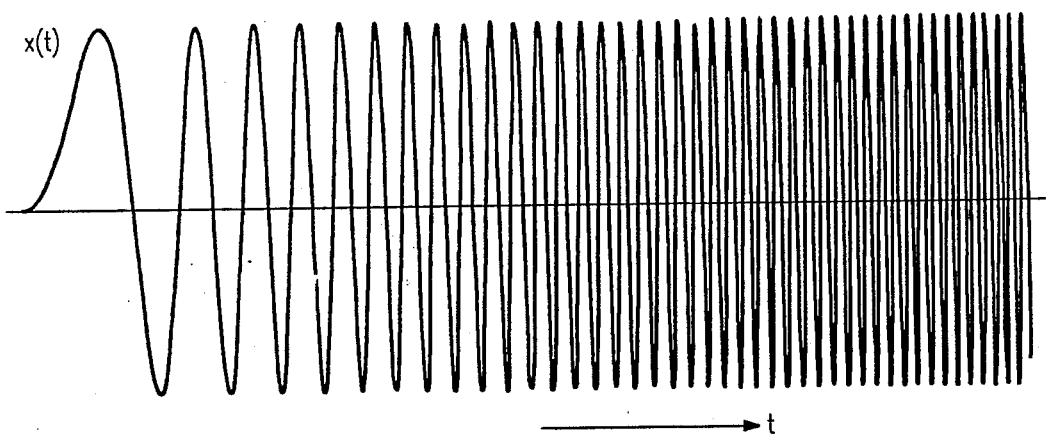
FIG. 4a is a schematic representation of a sign wave having a uniformly varying frequency over a time period.
Figure 4B:
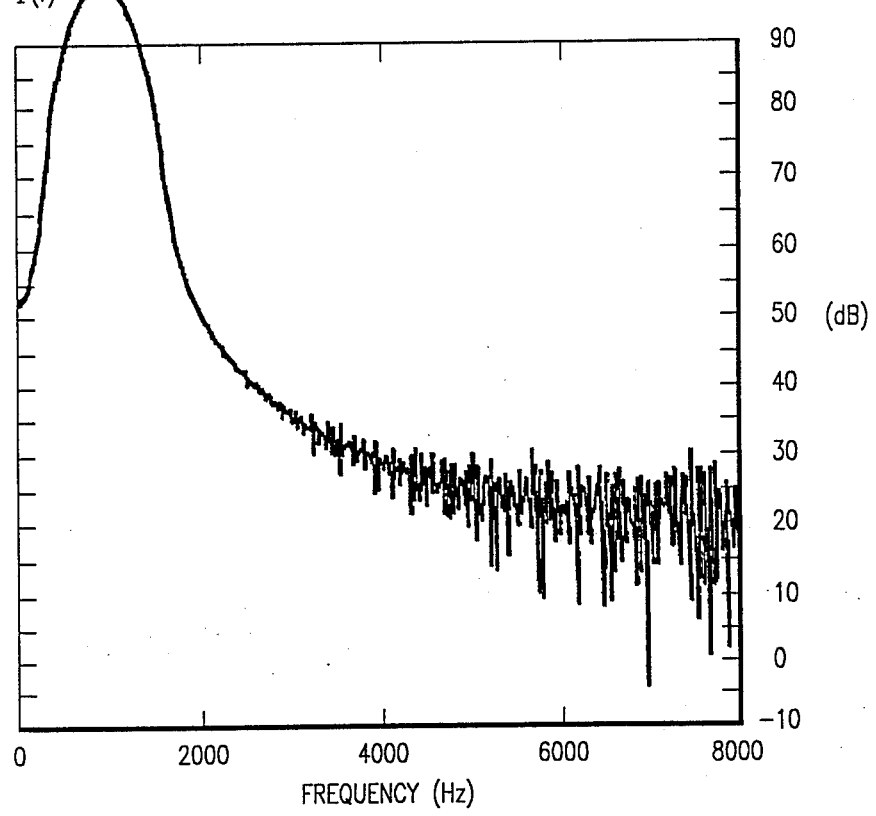
Figure 4C:
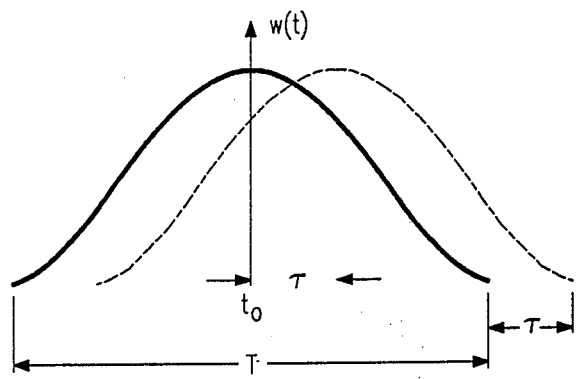
FIG. 4c is a schematic representation of a typical window which would be used in accordance with the present invention to process the signal illustrated in FIG. 4b.
Figure 4D:
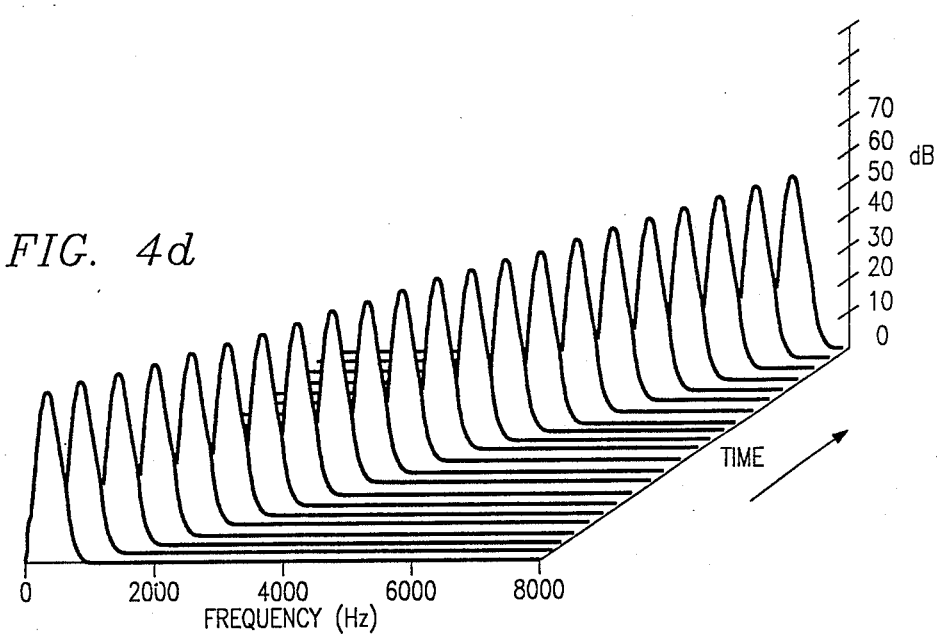
FIG. 4d is a schematic representation of the data derived by using the window represented in FIG. 4c to process the signal represented in FIG. 4a using a Fourier Transform in accordance with the present invention.

FIG. 2 shows a signal-averaged ECG with evident ventricular late potentials. The first step is to select a period of interest in the ECG to be analyzed. Although all or any portion of the ECG can and will often be analyzed in accordance with the present invention, assume that only the late potential period, $T_2$, is to be analyzed, for purposes of illustration. A limited window, i.e., 12-32 milliseconds of segment $T_2$ of the ECG is isolated by multiplying the ECG waveform with a selected window function. Just 'cutting out' the period of interest—i.e. not explicitly applying a window—is equivalent to multiplying the ECG waveform by a rectangular window, rect(n). However, this abrupt truncation has undesirable side effects, as will be seen later, and so a smoother window function such as the well known Blackman-Harris or Hamming window schematically illustrated in FIG. 4(c), is generally used.

The mean value of the ECG data in the time window to be transformed is usually not equal to zero. This mean value consists of two components. First, there is a dc component due to voltage drifts at the electrodes, or caused by the recording instrumentation. This is of no interest. Second, the ECG waveform itself has a non-zero mean value. This may be of interest. For example, a normal and a post-exercise ST segment waveform have different mean values. However, for consistency, the mean value in both cases should be referenced to the zero ECG value, i.e. the value in the TP interval of the ECG which represents zero heart action. Because the first (dc) component often predominates, it is usually advisable to subtract the mean value from the period of interest before Fourier transforming the ECG data in the window.

The discrete Fourier transform, X(k), is usually computed with a high speed computer algorithm known as the Fast Fourier Transform (FFT). The FFT requires that the number of samples making up the time domain waveform be a power of two (32, 64, 128 etc.). This is accomplished by "zero-padding": i.e. the input data to the FFT is augmented with zeros placed after the ECG data points.

Applying a window in the time domain and computing the power density spectrum via the FFT produces only an estimate of the true spectrum. Because the act of windowing in the time domain, known as tapering, is equivalent to low pass filtering the spectral waveform, this procedure is usually referred to as smoothing. The degree of smoothing obtained in this way cannot be varied. An added disadvantage of tapering is the arbitrary suppression of the waveform towards the ends of the window. This is an acute problem because of the timing of late potentials in the high resolution ECG, i.e. their close proximity to the main QRS.

The above description of classical Fourier transform analysis theoretically applies to processing a signal in which the frequency spectrum is constant over the time period of interest, i.e., the entire QRST segment, or as in the present illustration, period $T_2$ in FIG. 2, and prior attempts to use this approach have used a single window covering the time segment of interest. When analyzing late potentials, the observation interval ideally should be increased to get higher spectral resolution, but this means including QRS and/or ST segment samples as well as the late potential waveform in the time period for spectral analysis. The result of attempting to measure this time-varying late potential spectrum using Fourier procedures designed for segments which are spectrally non-variant with respect to time, as has previously been attempted by Cain, is that the power density spectrum obtained is an average of all the spectra that exist within the observation interval, i.e., the QRST segment of the ECG, and has little or no use in analyzing ECG data.

FIGS. $4_a$–$4_d$ contrast the prior methods and those or the present invention. FIG. $4_a$ represents a sine wave signal whose frequency increases continuously with time. This signal is called a swept sine wave. FIG. $4_b$ is a representation of the Fourier power density spectrum of the entire sweep signal period. It should be noted that the spectrum has no features that uniquely relate it to the swept sine wave. It is just the time average of all the frequency components of the signal. Note that increasingly higher frequencies are progressively underestimated due to the fact that, by definition, they exist for a shorter time period. FIG. $4_d$ shows the time-varying spectrum of the same swept sine wave, or the variations of energy in both time and frequency. This time-varying spectrum was obtained by placing a "short-time" window, represented in FIG. $4_c$, which has a time period (T) much shorter than the period of interest, i.e., the total period of swept sine wave. This window is placed at the start of the signal and by multiplying the signal by the value of the window, and a power density spectrum PDS is computed for the "portion" of the signal within the window and the values plotted on the frequency axis for the time on the time axis that is at the center of the window. The window is then shifted in time by a small amount ($\tau$), and another PDS spectrum is computed and plotted at the corresponding time. This procedure is repeated at time intervals ($\tau$) across the time period of interest. In the present case of analyzing ECG data, the entire QRST segment can be the time period of interest and can be processed in accordance with the present invention without adverse effects.

The ideal time-varying spectrum would be a continuous sequence of impulses along the diagonal as shown in FIG. $4_d$. However, the actual sequence of smeared spectra shown represents a compromise between the dynamic changes in time of the signal and the superior spectral resolution obtainable with longer observation periods. Dynamic changes in time of signal energy are better represented by a short window duration, whereas spectral resolution improves with a longer window duration. Formally, the spectral slice at time n0 of the time-varying spectrum of FIG. $4_d$ E(n,K), can be mathematically expressed as $$E(n_0,k) = \sum_{n=0}^{T-1} (x(n + n_0 - T/2) * w(n)) \exp(-j2\pi nk/N) \quad [12]$$

where w(n) is the window function, of length T samples, employed.

Figure 5:
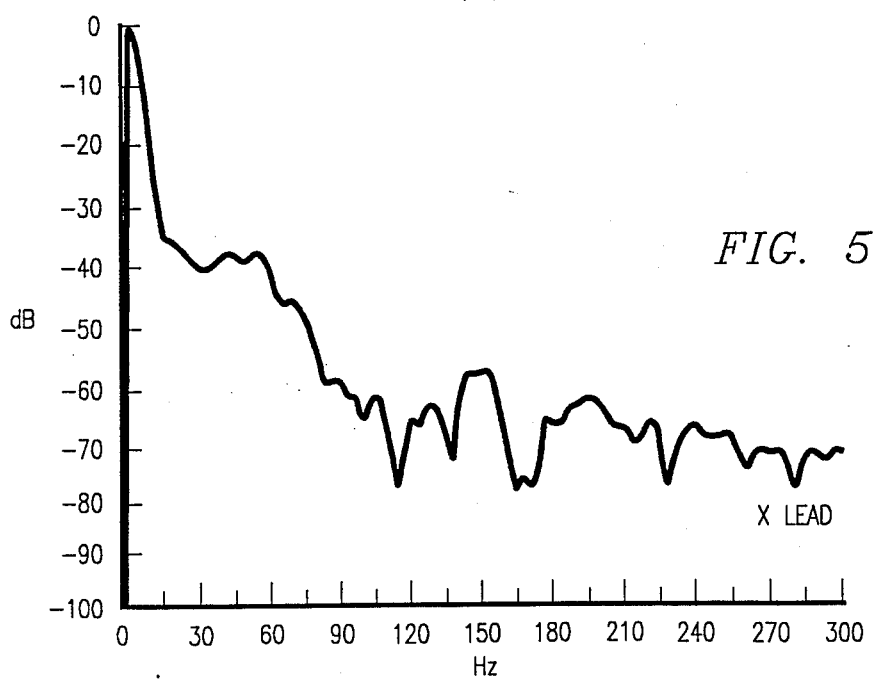
FIG. 5 is a graphical representation of the results of a Fourier Transform performed on the HRECG of FIG. 2.

FIG. $6_a$ illustrates a three dimensional surface in accordance with the present invention representing a time-varying spectrum of the signal-averaged ECG shown in FIG. 2. For comparison, the total power density spectrum for the corresponding portion of the QRS time segment of the signal-averaged waveform of FIG. 2 is shown in FIG. 5. The data representing the three dimensional surface of FIG. 6a was generated by frequency spectrum estimator calculations. The frequency spectrum estimations involved performing a initial Fast Fourier Transform calculation using conventional techniques on a 16 millisecond period or window which has been multiplied by the Hamming window function. This procedure was repeated after effectively sliding or shifting the window by a 2.0 millisecond interval. FIG. 6a illustrates 70 spectral templates. The time-varying spectrum reveals the variations of the spectra (i.e. the shape) with time, or the variation in spectral energy of the signal. Hence the term Spectro-Temporal Map (STM) is herein used as a description of the time-varying spectrum of selected ECG data in accordance with the present invention. The ECGSTM illustrates late potential activity in this subject with accurate identification of the beginning of the period $T_2$ of FIG. 2, compared with the unfiltered signal average. Note that the terminal portion of the QRS period, which can be identified separately from the late potentials, appears to have low-level continuous variations in the spectro-temporal energy, i.e., the shape of each successive spectral template, which is indicative that the late potentials start before the end of the QRS.

Figures 6B, 6C:
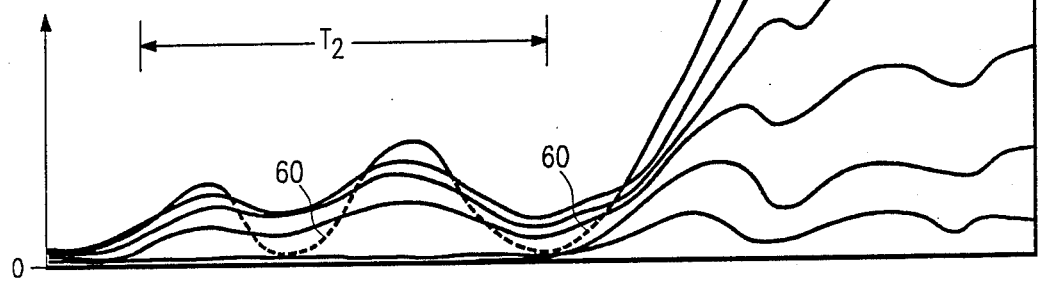

The ECGSTM of FIG. 6b was computed using the following procedure in accordance with the present invention to process HRECG which had a sample rate of 2,000 samples per second, i.e., 0.5 millisecond intervals.

1. The first derivative of entire time period of interest is obtained in accordance with the function $x(n)=x(n)-x(n-1)$ in order to reduce the predominantly low frequency energy of the ST segment waveform.

2. A data window time period is selected between 12–32 milliseconds, namely 16 milliseconds.

3. A time period $\tau$ over which the data window period is to be incrementally indexed is selected, typically 2.0 milliseconds.

4. The Hamming window function is applied to the portion of the signal within the windowed time period.

5. The windowed data is zero padded out to 512 data points.

6. A 512 point Fast Fourier Transform is performed to produce X(k).

7. A power spectrum $P(K)=|X(K)|^2$ is calculated which is the spectral contour and associated spectral template line of the ECGSTM for the time at the center of the applied window.

8. The data window is incremented by the selected time interval ($\tau$) of 2 milliseconds and steps 4–8 repeated to generate the remaining spectral contour line over the time segment of interest.

The exact values of the parameters for computing the STM, i.e., the values of T and $\tau$, are not of critical importance. For the STM of FIG. 6b, values of T=16 ms and $\tau=2$ ms were used. The basic shape and outline of the spectro-temporal map did not change significantly when T was varied over the range of 12–24 milliseconds and $\tau$ over the range of 1–4 milliseconds. Although the theoretical spectral resolution of each spectral template in the STM is poor, i.e., at T=16 ms, the theoretical effective spectral resolution, $B_e$, is only 225 Hz, the ECGSTM still contains repeatable, highly useful information when presented visually, and also contains information which can be used to automatically or manually calculate criterion which can be clinically shown to be indicative of late potentials or other categorical abnormalities.

The sliding window autoregressive method referred to as block 32 of FIG. 1 is based on the idea that the ECG signal under FFT analysis is autoregressive in structure: i.e. each future value can be found from a linear combination of past values. From the discussion of spectral resolution and windowing above, it can be seen that the FFT gives only an estimate of the true power spectrum. The FFT uses a specific mathematical model to depict the spectrum, namely a moving average model. As discussed previously, FFT analysis becomes less precise when high spectral resolution is desired from short time series. Another type of model, the autoregressive or AR model, is better suited to estimating power density spectra with sharp spectral features. The properties of AR models are best explained using Z-transform mathematics, and is described in detail in "*Numerical Recipes: The art of scientific computing.*" by Press et al Cambridge University Press, 1987.

An AR model is fitted not to the original signal, x(n), but to its autocorrelation function, r(n) as defined by equation[8]). The AR model has a number of terms or coefficients M, usually referred to as its order. Mathematically, the AR model is related to the autocorrelation function with M coefficients, $C_o$ to $C_m$, attempting to model the autocorrelation function of the original signal.

Typically M is much smaller than the number of samples, N, of the original signal x(n). However, the M-term AR model can actually generate an extrapolated autocorrelation function of more than N samples in length. It can be shown that the extrapolation achieved gives a maximum entropy estimate (MEM) of the autocorrelation function, in the sense understood by information theory. In other words, the AR model adds terms to the autocorrelation function that are not strictly measurable from the original N-sample signal. A number of computer algorithms exist to solve for the values of the AR model coefficients $C_o$ to $C_m$. The original algorithm was introduced by Burg in 1968 and subsequent variations on this algorithm have since appeared for use with specific types of signals.

Once the AR model has been obtained it is used to generate the extrapolated autocorrelation function, which is then Fourier transformed to obtain the AR power spectral estimate. The extrapolated autocorrelation function gives a higher resolution power spectrum. Therefore the power spectral estimate produced by the AR model would seem to be enhanced over the one given by the FFT. In practice, though, the apparent advantages of AR modeling via the maximum entropy method (MEM) are not always realized. From a historical perspective, MEM was developed to estimate the power spectra of sonar and speech waveforms where sharp spectral peaks with a short time interval between the peaks are anticipated. The main advantage of MEM is its ability to resolve sharp spectral features and to keep spectrally adjacent peaks distinct. Where narrow-band signals, possibly in the presence of noise, must be identified MEM gives superior spectral estimates, compared to the FFT approach. However, if no such distinctive spectral peaks are present, MEM offers no fundamental improvement over the FFT. In fact MEM may introduce artifacts into the spectral estimate in the form of spurious peaks. No concrete guidelines are available to assist in the choice of the order, M, of the AR model. Consequently values of M must be developed empirically for the class of signal-averaged ECG waveforms. Using different choices of M can cause spectral estimates of the same time domain signal to vary dramatically. Because of this the MEM approach to spectral analysis is inherently less stable than that of the FFT. In summary, MEM can reduce the spectral artifacts caused by windowing, but at the possible expense of destabilizing the estimated power spectrum.

Figure 7:
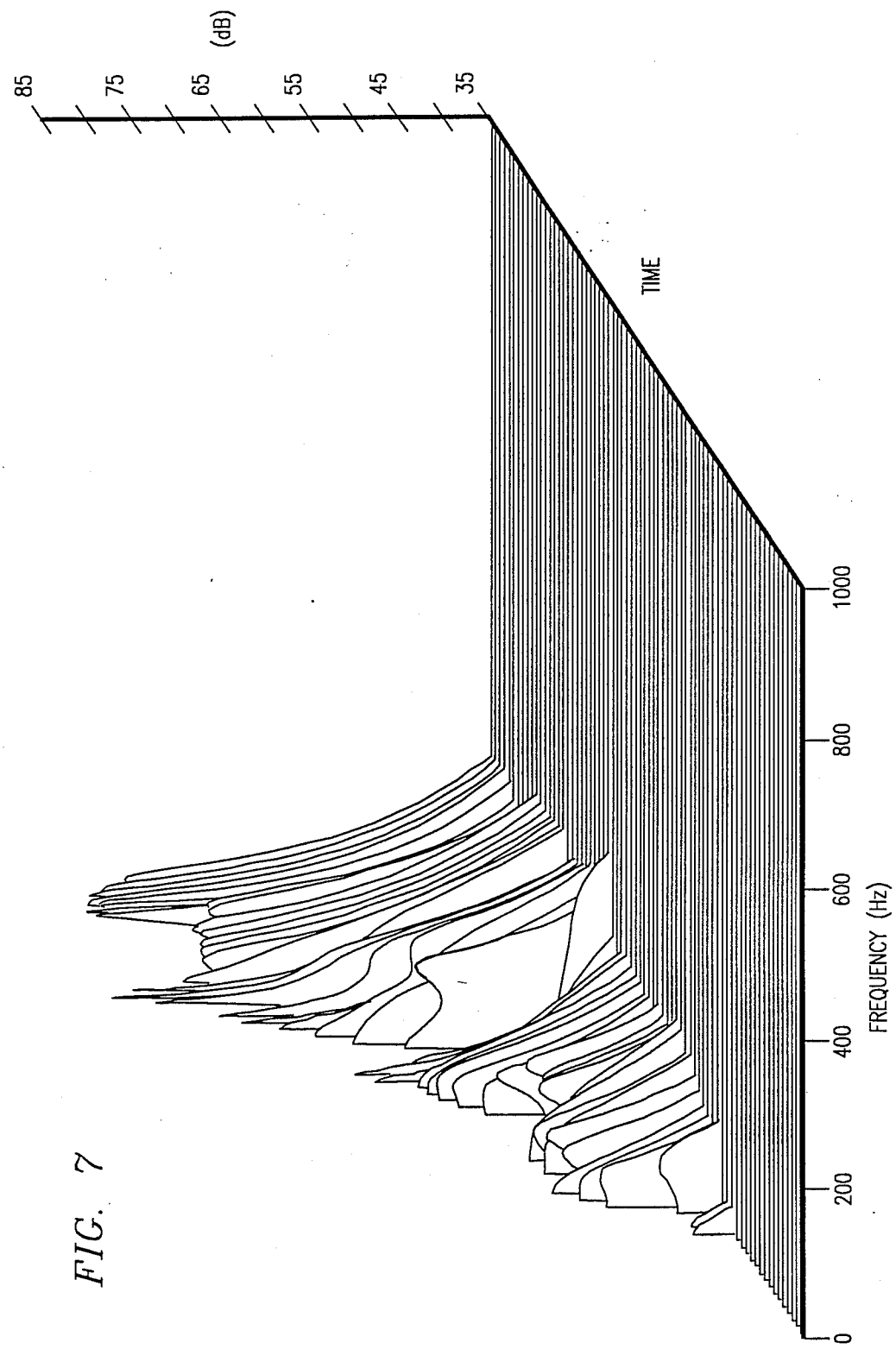
FIG. 7 is a schematic representation similar to FIG. 6a derived by processing the HRECG of FIG. 2 using the sliding window autoregressive embodiment of the present invention.

FIG. 7 illustrates the use of auto regressive (AR) techniques to compute MEM value which are presented as a spectrotemporal map of the signal averaged ECG of FIG. 2. Note that the MEM derived STM shown in FIG. 7 is plotted on a logarithmic scale, while the FFT derived STM OF FIG. 6(b) is plotted on a magnitude scale. Both STM's have been scaled individually in order to optimally present their spectral features. The MEM STM was computed with parameter values of T=16 ms and $\tau$=2 ms (similarly to the FFT STM) and using a 4th order AR model (M=4). The time-varying spectral features of the signal-averaged ECG are consistently reproduced by the FFT and MEM STM's. In both cases the end of the ventricular activity is readily indentifiable and the essential form of the STM's are very similar. The spectral edge frequencies (the highest frequency in each slice at which there is signal energy) are more clearly discernible in the MEM STM, due to the suppression of windowing artifacts.

The Sliding Window FFT frequency spectrum estimator and the Sliding Window Autoregressive frequency spectrum estimators referred to in calculation box 32 are special cases of more generalized frequency spectrum estimators such as the Wigner-Ville Distribution. The sliding window FFT and autoregressive techniques provide satisfactory results, but where additional resolution in the frequency domain is desired, the Wigner-Ville approach may be used. The Wigner-Ville approach is known in the signal processing art and is described in the article "Wigner-Ville-Spectral Analysis of Nonstationary Processes" by Martin and Flandren, IEEE Transactions on Acoustics, Speech, and Signal Processing, Vol. ASSP-33, No. 6, December 1985, Page 1461. This article, including the list of references cited therein, are all expressly incorporated by reference in this specification.

Any of the three methods of frequency spectrum estimation can produce the necessary three dimensional surface data used in the method and apparatus of the present invention. As previously mentioned, the surface data represented by the spectral templates produced by the frequency spectrum estimations of block 32 are conveniently stored in memory represented by block 40. The basic data derived from the frequency spectrum estimates constitute a series of constant time contour lines which, when projected onto the plane defined by the frequency amplitude coordinates define a geometric shape or "template" which contains valuable analysis information in both the shape and the area. The uses of which in accordance with the present invention will presently be described.

It is also often desirable, particularly for visual display, to develop additional sets of contour templates from constant frequency and constant amplitude contour lines on the data surface. Constant time templates can be selected at greater intervals than the frequency spectrum estimations were made, i.e., two milliseconds, for clarity of display, or if desired, could even be made at closer intervals than the sampling rate by interpolation. Similarly, constant frequency templates can be made by selecting an appropriate frequency interval such as 25 Hz, for example, and connecting all points of the three dimensional surface having such constant frequencies. These constant frequency lines are illustrated in FIG. 6(b) and also define a set of constant frequency templates. Similarly, constant amplitude contour lines and templates can be produced by connecting all data points on the surface having the same amplitudes, and a set of these are illustrated in FIG. 6b. Any of these three sets of contour templates can then subsequently be processed by any of the procedures represented in blocks 44, 46, 48 or 50, as desired.

As previously mentioned FIG. 6(a) is a three dimensional visual representation of the data surface for the high resolution ECG of FIG. 2, which is illustrated using the constant time or "spectral templates", which conveniently may be the data produced by the computations of the block 32 mode for each time position of the sliding window, i.e., at 2.0 millisecond intervals of time. The three dimension surface presented by these spectral templates illustrates that the general shape of these templates is substantially the same for the normal portion of the RS segment. However, at the onset of time $T_2$, which represents late potentials, there is a dramatic change in the shape of these templates, and changes continue to occur throughout the late potential time segment.

FIG. 6b is representative of a set of constant frequency templates superimposed upon the plane defined by time and amplitude axes. The set is limited in number for clarity purposes. However, during the late potential time period $T_2$, the crossing of the contour lines, as represented by the dotted outlines 60 of the low frequencies behind the intermediate frequencies, clearly reveals the major changes in the shape of the three dimensional surface, which indicate that the frequency distribution of the late potential segment is substantially different than that of the normal QRS segment. Similarly, FIG. 6c is a representation of constant amplitude contour lines projected against the plane defined by the time and frequency axes and again reveals in the regions 62 the points at which there is a dramatic change in the cross-sectional shape and thus the spectral frequencies. The spectral energy above about 50 Hz in the absence of lower frequency energy is clearly indicative of late potentials.

As mentioned, any of the contour lines defining the contour templates can be displayed on the visual display screen 20, either simultaneously or separately, or in any combination thereof, to assist in clearly delineating the undulating three dimensional surface representing the ECGSTM. It is also quite useful to provide the capability of moving the viewpoint for the three-axes display to any position relative to the image. Of course, by orienting the viewpoint parallel to any one of the three axes, the contour lines, and thus the corresponding templates, can be projected onto the appropriate plane defined by the other two axes, such as illustrated in FIGS. 6b and 6c.

Although FIGS. 6a, 6b and 6c illustrate that late potentials are readily evident from the display of the three dimensional surface, and that a physician or other skilled operator, will certainly utilize this as a major input toward any professional decision, it is always desirable to have quantified indicators related to clinical data which can be automatically developed from predetermined criteria, or from manually selected data, as a further diagnostic tool.

Adjacent Template Calculation

Figure 8:
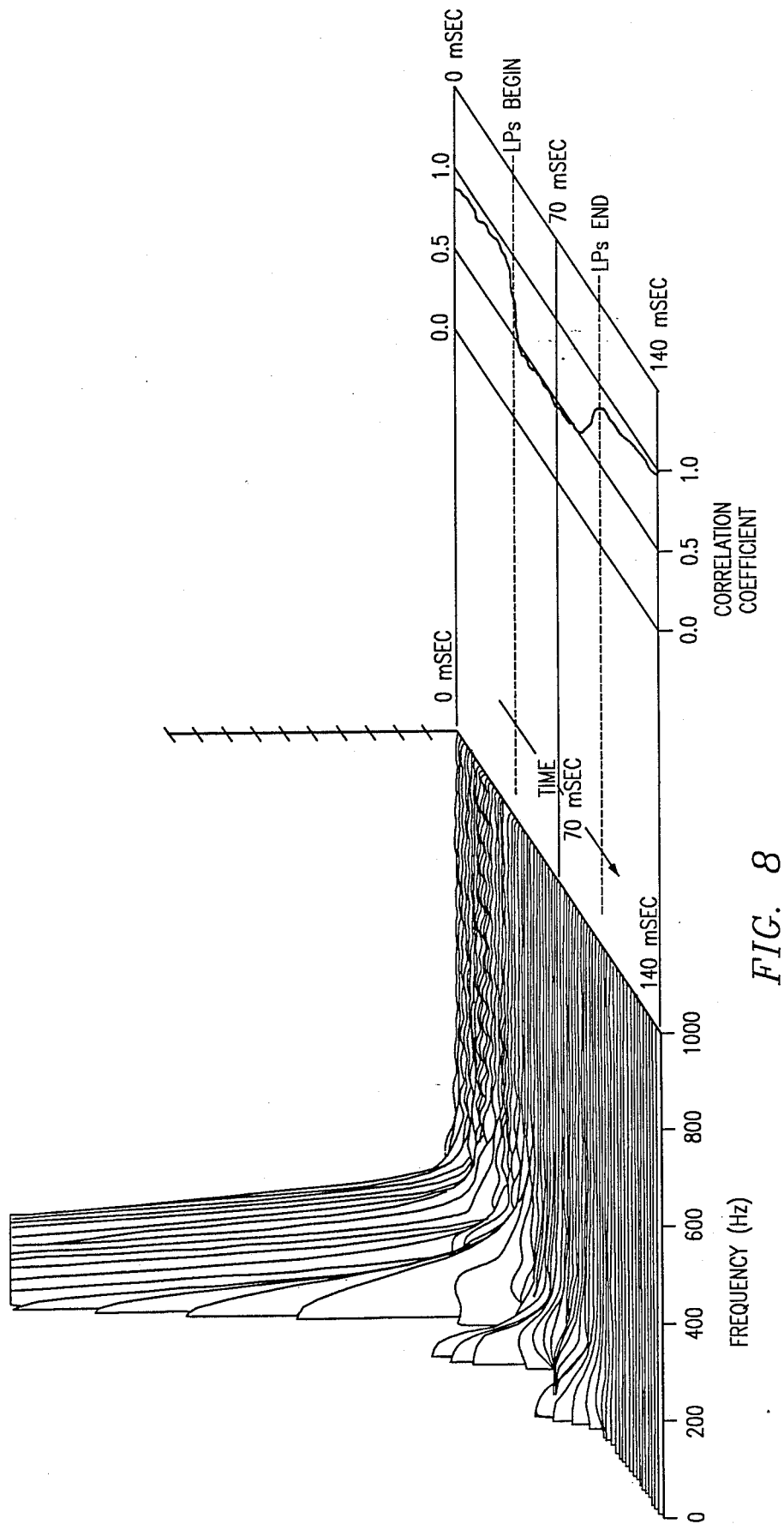

Thus, an adjacent template correlation analysis can be performed by the CPU and the data stored as represented by the block 44. The adjacent template correlation involves comparing adjacent, or otherwise space related templates, for correspondence in shape, area or other characteristics as desired. Perhaps the most useful correlation involves that of comparing the shape of adjacent spectral templates of the set represented in the ECGSTM of FIG. 6a. Such a correlation can best illustrate the change in frequency content with respect to time. Such a correlation is illustrated in FIG. 8 where a correlation coefficient is plotted with respect to time for the ECGSTM of FIG. 6a. This correlation coefficient can be produced by computing, at each frequency interval of the respective templates, the cross correlation coefficient of the two templates. The corresponding frequency points on adjacent templates can be compared in the true amplitudes, or the templates can be normalized to the peak amplitude of the two templates being compared, a predetermining value, or any other desired normalizing criteria.

Residual Spectra Analysis

Figure 9A:
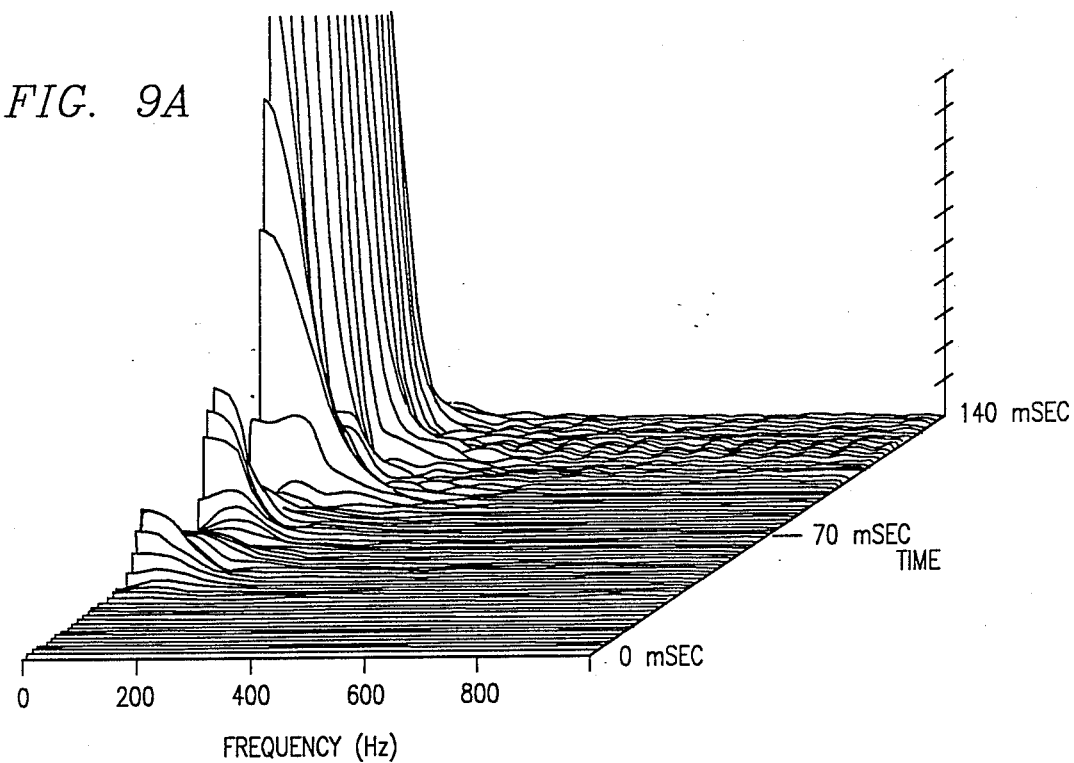
Figure 9B:
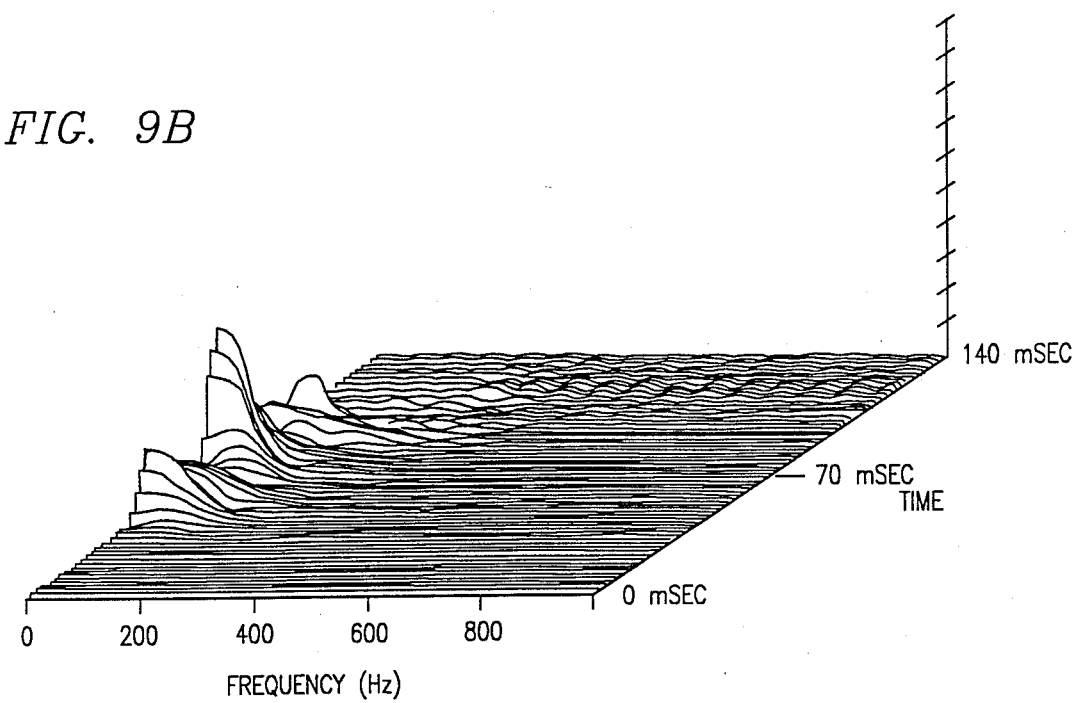

Another form of template correlation may be described as residual spectra analysis, which is represented in block 46. This procedure is very similar to the adjacent template correlation described in 44 except that the individual difference values derived for the respective frequency points is maintained and the result displayed as a series of constant residual frequency templates as illustrated in FIG. 9b. In this procedure, the peak amplitude values, or the integrated areas of each spectral template, are normalized to a value of 1.0, and the discrete normalized values of adjacent spectral values are subtracted and displayed as a residual template. FIG. 9A, which is equivalent to the display of FIG. 6a, illustrates the ECGSTM to which the residual spectra analysis procedure is conducted. FIG. 9a is referred to as an "original" STM. Thus, FIG. 9b can be referred to as a "residual" STM. It will be noted that because the spectral templates for the main portion of the QRS function are virtually identical in shape, these features essentially disappear from the residual STM of FIG. 9b. On the other hand, the spectral templates in the spectrally time variant late potentials region $T_2$ are quite pronounced and clearly indicate the presence of the late potentials, as well as indicating onset/offset and total duration of the late potential time segment $T_2$, even where the late potentials and QRS segments tend to overlap. This provides an analysis tool which can detect most of the late potentials even though intermingled with a normal length QRS segment or a prolonged QRS segment of the type caused by bundle branch block. Also, the onset and ends of the QRS segment produces a major change which is evident on the type of STM.

Spectral Edge Frequency

Figure 10:
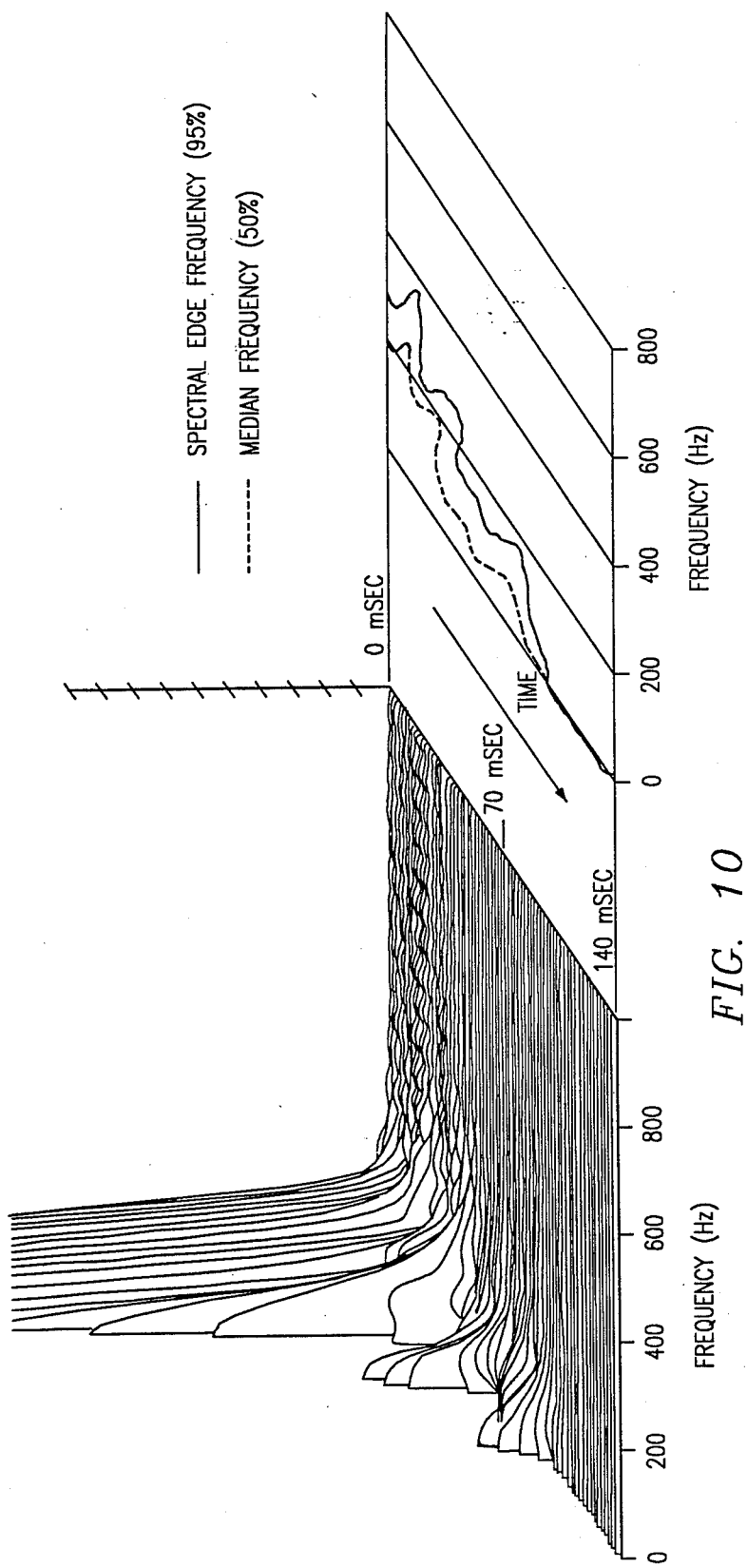

Another useful tool in evaluating the spectral contour templates is to produce a plot of various characteristics of each successive template of a set with respect to time, as illustrated in FIG. 10 which relates to the spectral templates. These plots can be a measure of the spectral edge as defined by the frequency below which some percentage of the total instantaneous energy lies, such as 95%, the median frequency, the mean frequency, or any other desired measure of the templates definable along the frequency axis of the templates. The plots of FIG. 10 where generated from the ECGSTM data displayed in FIG. 6a.

Area or Volume Calculations

Another very useful set of calculations which can be performed with regard to the ECGSTM is that of calculating the area of a template within proscribed limits. The proscribed areas of a number of templates can also be multiplied by a time unit and the products summed to provide a volume. For example, a measure of the RMS value of the signal for a given time increment is a function of the volume under the surface as proscribed by the time increment. The portion of a spectral template above a designated frequency is equivalent to the result of a high pass filter, that below a designated frequency is the equivalent result to a low pass filter, and that between designated frequencies is the equivalent result to a bandpass filter. The area computations are most commonly made on the constant time or spectral templates, including the residual spectral templates of FIG. 9b. However, these computations can be made on any desired template or set of templates.

CPU Calculations

In addition to controlling the overall operation of the system, the CPU can, under automatic or keyboard entry, perform routine calculations from the data previously calculated and stored as represented in boxes 36, 44, 46, 48 and 50. Of course, the CPU, through the three axis display generator, can cause any of the data accessible through the bus 30 to be displayed. In addition, computed numerical data can be displayed in an area schematically represented on the right-hand side of the visual display.

For example, the QRS onset can be automatically calculated by detecting the first spectral template having a preselected area, typically above a preselected minimum amplitude. Or, if desired, the onset can be automatically selected as a time point having a predetermined relationship to the first occurrence of a predetermined volume under the surface, which is essentially an RMS power calculation. Termination of the QRS, including any late potentials, can be selected by the same techniques but proceeding in reverse time direction. Of course, either the QRS onset or the QRS end can be very easily selected manually by observing this point on the visually displayed information of the ECGSTM, or the residual STM, using the desired contour lines observed from any appropriate viewpoint. The manual selection of the data point is conveniently selected by moving a cursor on the display screen to the desired data point, and then producing a data select command in the convention manner employed in computer technology. The QRS duration can then be readily calculated upon command and the numerical value displayed.

The onset of any late potentials can be, of course, also readily visually detected from the ECGSTM display or from the other secondary evaluation displays such as the adjacent template correlation, Residual STM or spectral frequency edge, median or mean type data. Also, the total power for a predesignated time period in advance of the end of the QRS+LP segment can easily be determined simply by measuring the volume under the spectrotemporal surface for that time period, which is a measure of the RMS power. Further, the volume being measured can be limited to that above a predetermined frequency, thus in effect passing the signal through a high-pass filter without the deleterious phase shift properties inherently associated with the filtering process. Of course, since the signal data, the signal averaged data, or the vector sum data is available in data storage 27, all conventional calculations and display functions of this data can also be carried out by the central processing unit 34 using appropriate programs (not illustrated).

Figure 11A:
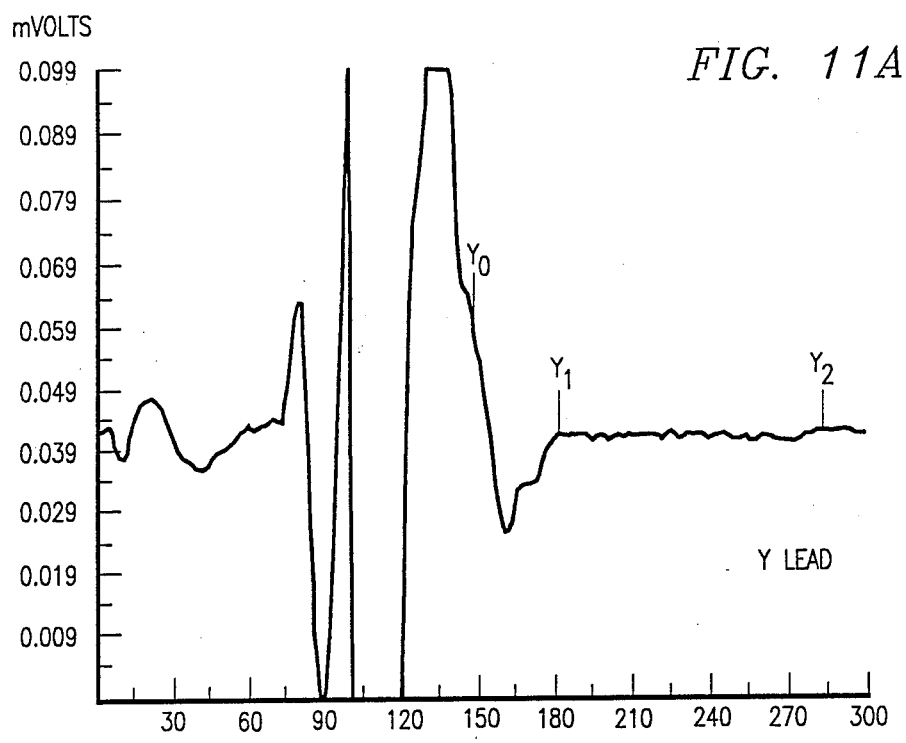
FIG. 11a is a schematic representation of a graph derived using prior art techniques of reverse filtering the Y lead of a HRECG for the purpose of detecting late potentials.
Figure 11B:
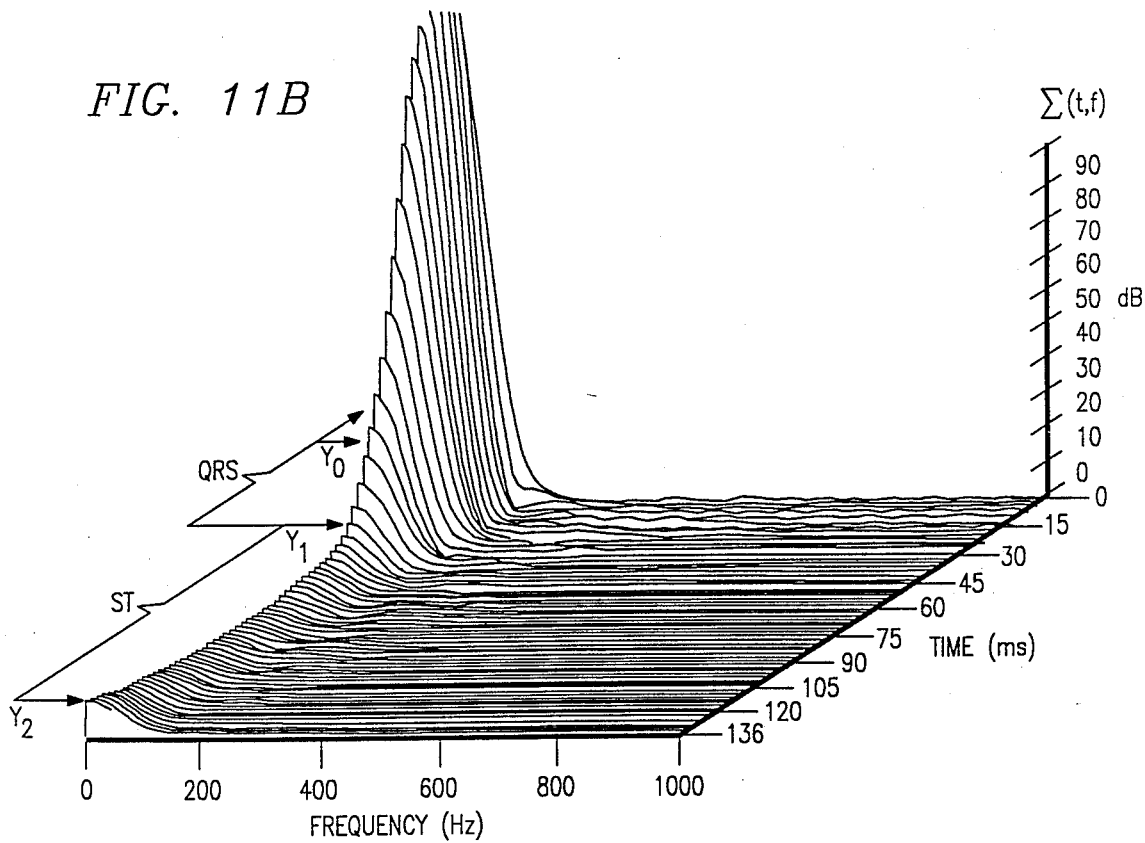
FIG. 11b is a schematic, three dimensional graph representing a three dimensional surface formed by the contour lines of a set of constant time spectral templates indicating the absence of late potentials.

The preferred embodiment of the method of the present invention was used to evaluate high resolution ECG's of patients previously determined to have late potentials indicative of the risk of acute arrhythmia, as compared to others known to be free of such late potentials. FIGS. 11a and 11b relate to a patient known to have a "normal" ECG free of late potentials. FIG. 11a is a graphical representation of the Y-lead signal averaged, high resolution ECG of a normal heart to which a high pass filter has been applied in bidirectional time order in accordance with the best established prior art method of detecting late potentials. FIG. 11b is a spectro-temporal map (STM) of the same Y-lead, HRECG, in accordance with the method of the present invention as described in connection with FIG. 6a. From the normal ECGSTM of FIG. 11b, it is noted that there is virtually no change in the shape of the spectral templates in the $Y_0$-$Y_1$ segment and within the ST segment from $Y_1$-$Y_0$, and that the transition from the QRS to the ST segment is characterized by small changes in the shape of the spectral templates, i.e., high correlations.

Figure 11C:
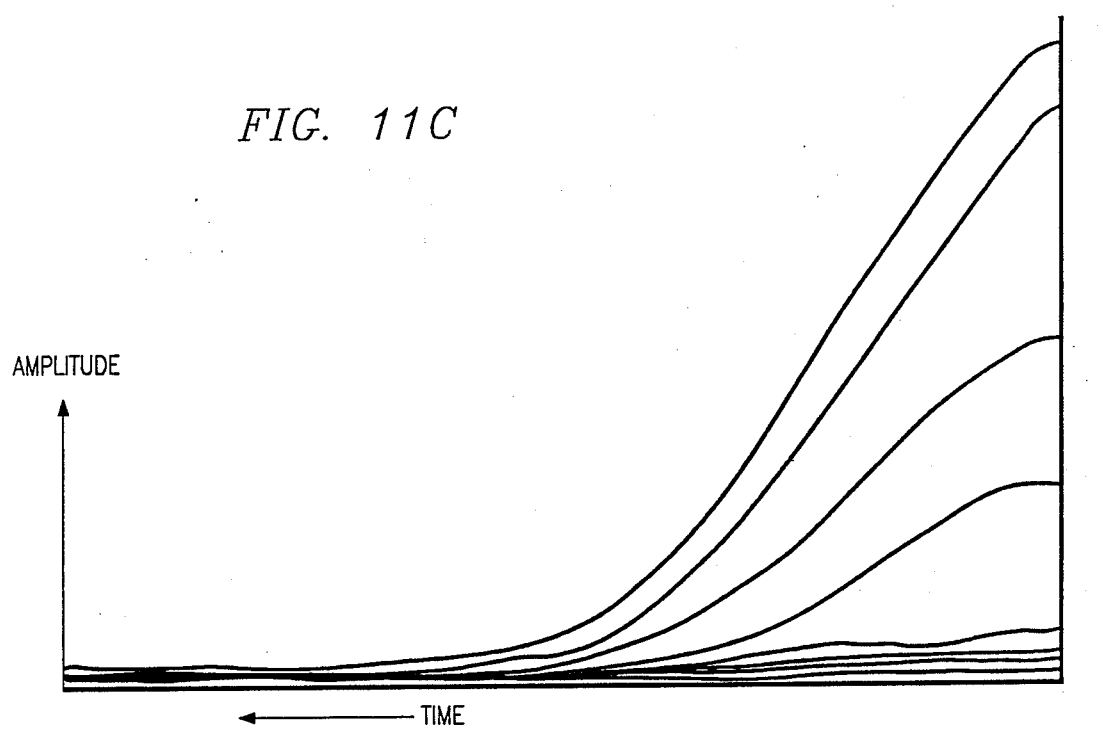
Figure 11D:
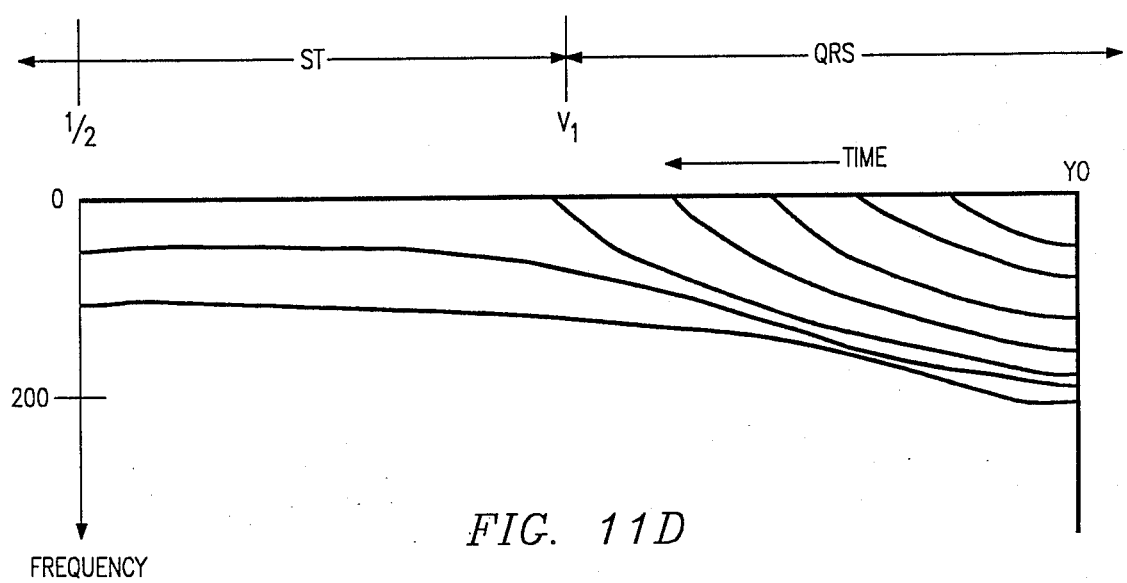

FIGS. 11c and 11d are also provided for the normal ECGSTM for comparison with the corresponding FIGS. 6c and 6d of the ECGSTM which includes late potentials. FIG. 11c represents the constant frequency templates superimposed against the plane of the time and amplitude axes, while FIG. 11d discloses the constant amplitude templates superimposed on the plane of the time and frequency axes. The contrast between the two ECGSTM presentations clearly illustrates the diagnostic power of the presentation in accordance with the present invention with regard to late potentials.

FIG. 12a, 12b and 12c relate to a patient who presented with ventricular tachycardia, after a mild myocardial infarction, and had sustained monomorphic ventricular tachycardia during programmed electro physiological study. FIG. 12a illustrates unfiltered, signal averaged X, Y and Z leads which have herein been termed high resolution ECG's. FIG. 12b is a graphical representation of the vector magnitude of the X, Y, Z leads of FIG. 12A which has been bidirectionally filtered with a 25 Hz, fourth order high pass filter in accordance with prior art techniques, (the display scale is 1.0 and the vector type is the square root of the sum of $X^2+Y^2+Z^2$) and FIG. 12c is a spectro-temporal map of the unfiltered lead X of the HRECG of FIG. 12a. When compared to FIG. 12b, FIG. 12c indicates significant spectro-temporal energy changes in the terminal part of the QRS. This is in contrast to the representation of FIG. 12b, where the QRS duration is 112 milliseconds, the root-mean-square voltage of the terminal 40 milliseconds is 32 microvolts, the mean voltage of the terminal 40 milliseconds is 33 microvolts and a duration of the low amplitude signal less than 40 microvolts is 30 milliseconds, which by previous published standards would indicate the absence of late potentials because all parameters are outside the abnormal range. Thus, it is clear that the STM approach of FIG. 12c can at least in some instances clearly indicate late potentials not previously detectable using established techniques.

Figure 13A:
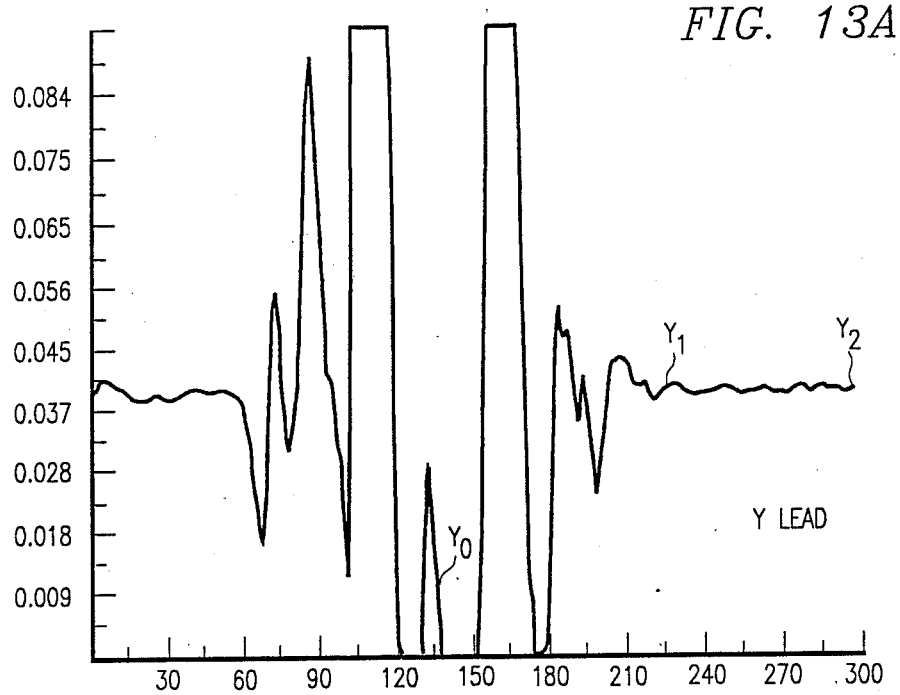
FIG. 13a is a schematic graph of a Y lead HRECG bidirectionally high pass filtered using prior art techniques for detecting late potentials.
Figure 13B:
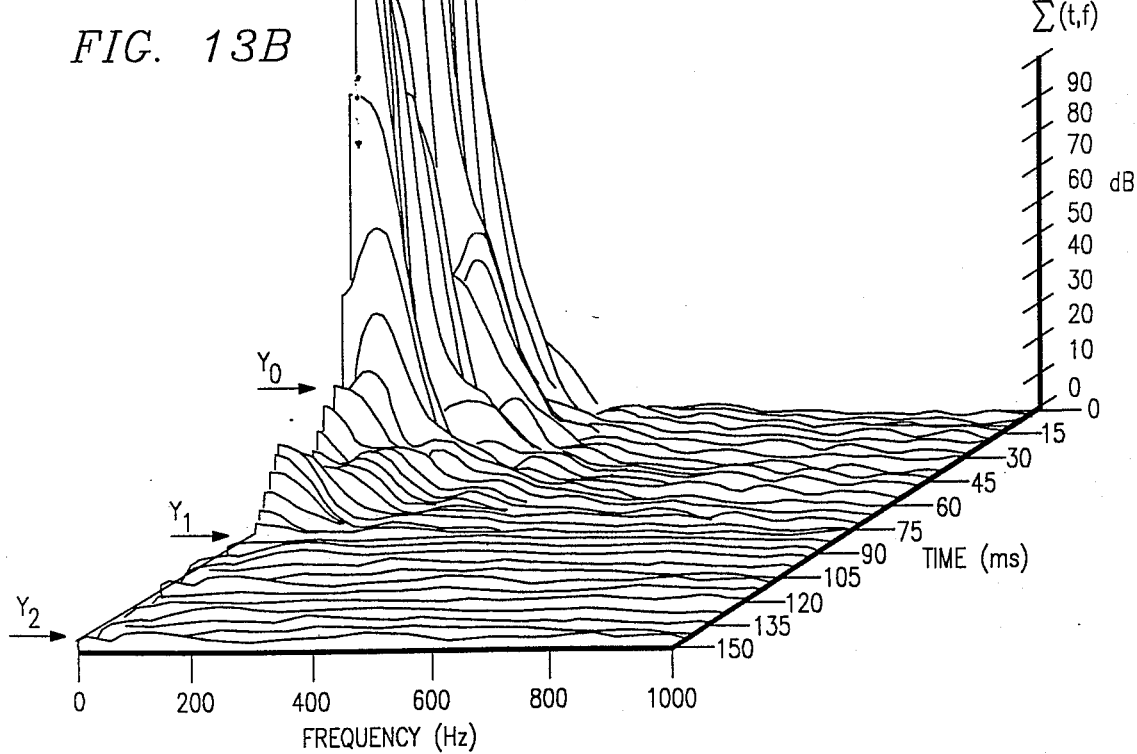

FIG. 13a and 13b relate to a patient with marked spectro-temporal energy changes in a terminal part of the QRS. FIG. 13a illustrates the 25 Hz bidirectionally high pass filtered Y-lead, HRECG for the patient. FIG. 13b is an STM of the same, but unfiltered, Y-lead HRECG. It may be observed that there are significant changes in the spectro-temporal energy well within the QRS complex which suggests at least the possibility that abnormal depolarization is also taking place during the period of major ventricular activation.

Although preferred embodiments of the invention have been described in detail, it is to be understood that various changes, substitutions and alterations can be made therein without departing from the spirit and scope of the invention as defined by the appended claims.

What is claimed is:

1. The system for evaluating a electrocardiogram (ECG) of a patient which comprises:
    means for calculating from the ECG and storing digital data defining a three dimensional graphic surface representative of the spectral frequency of the ECG in which the first axis is the time domain of the ECG, the second axis is the frequency domain, and the third axis is representative of the amplitude or power domain;
    means for displaying the surface in a three dimensional visually discernible presentation; and
    means for producing visually discernible indicia on the surface selected to reveal predetermined characteristics of the HRECG useful in medically evaluating the patient.

2. The system of claim 1 wherein the means for displaying the surface displays a set of templates defined by the surface.

3. The system of claim 2 wherein the set of templates is a set of spectral templates.

4. The system of claims 2 or 3 further comprising means for producing a measure of degree of correlation of relative shapes of at least two templates of the set spacially related one to the other in a selected manner.

5. The system of claim 4 wherein the degree of correlation is determined for adjacent templates of a selected set of templates and presented as a visual image related to the time domain axis of the surface.

6. The system of claim 5 wherein the degree of correlation is a correlation factor comprising a discrete value plotted with respect to time.

7. The system of claim 6 wherein the degree of correlation is a residual area template for each template pair and the residual area templates are displayed as a set in a three dimensional image.

8. The system of claim 1 or 2 further comprising means for producing a value with respect to the time domain representative of a selected attribute of the frequency spectrum at the corresponding point in time and displaying a set of such values with respect to time.

9. The system of claim 8 wherein the selected attribute is the spectral edge frequency.

10. The system of claim 8 wherein the selected attribute is the mean or median frequency.

11. The system of claims 1, 2 or 3 further comprising means for computing a value representative of the total area under the surface for a selected point on the time axis.

12. The system of claim 11 further comprising means for computing a value representative of the total volume defined by the surface and selected limits of time.

13. The system of claims 11 or 12 further including means for computing a series of values and selecting the first occurring value above a predetermined value as a reference point in time of the ECG.

14. The system as in one of claims 1-13 further comprising means for selectively, under operator control, rotating the axes of the visual presentation of the surface.

15. The system of claim 14 further comprising means for, under operator control, selecting different visually discernible indicia.

16. The system of claim 15 wherein the means under operator control include means for selectively displaying data points of a surface lying in a plane passing through said graphic surface.

17. The system of claim 15 or 16 wherein the means under operator control includes means for selecting lines indicating data points on, or equidistance from, a selected plane.

18. The system of claim 17 further comprising means for performing computational manipulation of the data defining the surface lying in a plane passing through said graphic surface to determine preselected values of interest of the data.

19. The system of claim 17 or 18 further comprising indicia means under control of the operator for selecting points on the display for inputting data to be used in computational manipulation of data.

20. The system of claim 18 wherein the preselected values include values indicative of onset and offset of the QRS segment of the HRECG and provide a measure of the overall time duration of the QRS segment.

21. The system of claim 20 wherein the preselected values include, for each time increment, a value equal to a predetermined percent of total spectrum power within predetermined frequency limits.

22. The system of claim 18 wherein the preselected values include at least one set of contour templates, each contour template being all values of a surface having the same constant predetermined value for one of the axes, and each successive template of the set having a predetermined value which is incrementally greater than the said predetermined value of the preceding template.

23. The system of claim 22 wherein each contour template has a constant time value.

24. The system of claim 22 wherein each contour template has a constant frequency value.

25. The system of claim 22 wherein each contour template has a constant power value.

26. The system as in one of claims 22-25 further comprising means for progressively comparing each template of at least a portion of the set of templates to the next adjacent template of the set to produce a correlation function and displaying the correlation function with respect to the respective constant values of the template set.

27. The system of claim 26 further comprising means for normalizing each successive template with respect to the adjacent template with which it is correlated such that the correlation value is primarily related to the templates shape.

28. The system of claim 26 or 27 further comprising means for automatically selecting predetermined events based on the first occurrence of a correlation value of predetermined magnitude.

* * * * *